US012662710B2

(12) United States Patent
Yamamoto et al.

(10) Patent No.: US 12,662,710 B2
(45) Date of Patent: Jun. 23, 2026

(54) METHOD FOR DETECTING SINGLE-STRANDED RNA VIRUS

(71) Applicant: EIKEN KAGAKU KABUSHIKI KAISHA, Tokyo (JP)

(72) Inventors: Machiko Yamamoto, Shimotsuga-gun (JP); Kota Yokono, Shimotsuga-gun (JP); Syouhei Semba, Shimotsuga-gun (JP); Satoru Michiyuki, Otawara (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 890 days.

(21) Appl. No.: 17/904,897

(22) PCT Filed: Feb. 24, 2021

(86) PCT No.: PCT/JP2021/006907
§ 371 (c)(1),
(2) Date: Aug. 24, 2022

(87) PCT Pub. No.: WO2021/172370
PCT Pub. Date: Sep. 2, 2021

(65) Prior Publication Data

US 2023/0175079 A1     Jun. 8, 2023

(30) Foreign Application Priority Data

Feb. 27, 2020     (JP) ................................. 2020-031780

(51) Int. Cl.
*C12Q 1/6844*      (2018.01)
*C12Q 1/6876*      (2018.01)
*C12Q 1/70*        (2006.01)
(52) U.S. Cl.
CPC ........... *C12Q 1/701* (2013.01); *C12Q 1/6844* (2013.01)
(58) Field of Classification Search
None
See application file for complete search history.

(56) References Cited

FOREIGN PATENT DOCUMENTS

| | | |
|---|---|---|
| CN | 102260733 A | 11/2011 |
| CN | 103074445 A | 5/2013 |
| CN | 106222298 A | 12/2016 |
| CN | 107236826 A | 10/2017 |
| JP | 2007000040 A | 1/2007 |
| WO | 00/028082 A1 | 5/2000 |
| WO | 02/024902 A1 | 3/2002 |
| WO | 2018/042598 A1 | 3/2018 |

OTHER PUBLICATIONS

Lee et al. One-Pot Reverse Transcriptional Loop-Mediated Isothermal Amplification (RT-LAMP) for Detecting MERS-CoV. Front. Microbiol., 2017, 7: 2166.*
Kurosaki et al. Development and Evaluation of a Simple Assay for Marburg Virus Detection Using a Reverse Transcription-Loop-Mediated Isothermal Amplification Method. Journal of Clinical Microbiology, 2010, 48: 2330-2336.*
Yang et al., "Detection methods for milk pathogenic bacteria by loop-mediated isothermal amplification", BioScience Trends, Dec. 31, 2014, pp. 316-321, vol. 8(6).
Xie et al., "Rapid diagnosis of H5subtype avian influenza virus by RT-loop-mediated isothermal amplification", Chin J V et Sci, Jan. 15, 2010, pp. 41-45, vol. 30(1), English Abstract.
European Patent Office, Extended European Search Report issued in European Patent Application No. 21759577.6, Feb. 14, 2024, pp. 1-6.
Ghaith, Duaa' Muhammad, "Development of a reverse transcription loop-mediated isothermal amplification assay for rapid detection of foot-and-mouth disease virus", Joint Biotechnology Master Program, Palestine Polytechnic University and Bethlehem University, Aug. 2018, pp. 1-69.
Ma et al., "Flower-like ZnO nanostructure assisted loop-mediated isothermal amplification assay for detection of Japanese encephalitis virus", Virus Research, Jan. 27, 2017, pp. 34-40, vol. 232.
Chen, Lei et al., "A Novel RT-LAMP Assay for Rapid and Simple Detection of Classical Swine Fever Virus", Virological Sinica, 2010, pp. 59-64, vol. 25(1).
Patent Cooperation Treaty, International Search Report issued in PCT/JP2021/006907, Apr. 27, 2021, pp. 1-2.
Patent Cooperation Treaty, Preliminary Report on Patentability issued in PCT/JP2021/006907, Sep. 9, 2022, pp. 1-5.

* cited by examiner

*Primary Examiner* — Nianxiang Zou
(74) *Attorney, Agent, or Firm* — Morgan, Lewis & Bockius LLP

(57) ABSTRACT

A method for detecting a single-stranded RNA virus in a sample includes: bringing a primer set into contact with a sample to perform a RT-LAMP reaction, wherein the primer set is designed based on a nucleotide sequence of a target RNA and a nucleotide sequence of a nucleic acid complementary to the target RNA, and includes following (i) to (v): (i) an FIP primer; (ii) a BIP primer; (iii) an F3 primer, which is an outer primer; (iv) a B3 primer, which is an outer primer; and (v) one or more additional outer primers, each additional outer primer having the same nucleotide sequence as an arbitrary region present on a 5' terminal side from the region B3 or the region F3 in the nucleic acid complementary to the target RNA. According to the present invention, a single-stranded RNA virus can be detected with high sensitivity.

4 Claims, 2 Drawing Sheets
Specification includes a Sequence Listing.

SEQUENCE LISTING

<160> NUMBER OF SEQ ID NOS: 62

<210> SEQ ID NO 1
<211> LENGTH: 411
<212> TYPE: RNA
<213> ORGANISM: Artificial sequence
<220> FEATURE:
<223> OTHER INFORMATION: modified sequence of DENV3 capsid

<400> SEQUENCE: 1
guaauacgac ucacuauagg gaguuguuag ucuacgugga ccgacaagaa caguuucgac      60
ucggaagcuu gcuuaacgua gugcugacag uuuuuuauua gagagcagau cucugaugaa      120
caaccaacgg aaaaagacgg gaaaaccguc uaucaauaug cugaaacgcg ugagaaaccg      180
ugugucaacu ggaucacagu uggcgaagag auucucaaaa ggauugcuga acggccaagg      240
accaaugaaa uugguuaugg cguucauagc uuuccucaga uuucuagcca uuccaccaac      300
agcaggaguc uuggcuagau ggggaaccuu caagaagucg ggggccauua agguccugaa      360
aggcuucaag aaggagaucu caaacaugcu gagcauuauc aacaaacgga a      411

<210> SEQ ID NO 2
<211> LENGTH: 21
<212> TYPE: DNA
<213> ORGANISM: Artificial sequence
<220> FEATURE:
<223> OTHER INFORMATION: DENV3_F3

<400> SEQUENCE: 2
cttaacgtag tgctgacagt t      21

<210> SEQ ID NO 3
<211> LENGTH: 18
<212> TYPE: DNA
<213> ORGANISM: Artificial sequence
<220> FEATURE:
<223> OTHER INFORMATION: DENV3_B3a

<400> SEQUENCE: 3
ctgctgttgg tggaatgg      18

<210> SEQ ID NO 4
<211> LENGTH: 48
<212> TYPE: DNA
<213> ORGANISM: Artificial sequence
<220> FEATURE:
<223> OTHER INFORMATION: DENV3_FIPv4

<400> SEQUENCE: 4
tctcacgcgt ttcagcatat tgagagagca gatctctgat gaacaacc      48

<210> SEQ ID NO 5
<211> LENGTH: 42
<212> TYPE: DNA
<213> ORGANISM: Artificial sequence
<220> FEATURE:
<223> OTHER INFORMATION: DENV3_BIPv6

<400> SEQUENCE: 5
tggcgaagag attctcaaga ggactagaaa tctgaggaaa gc      42

<210> SEQ ID NO 6
<211> LENGTH: 20
<212> TYPE: DNA
<213> ORGANISM: Artificial sequence

```
<220> FEATURE:
<223> OTHER INFORMATION: DENV3_LF

<400> SEQUENCE: 6
ttcccgtctt tttccgttgg                                            20

<210> SEQ ID NO 7
<211> LENGTH: 17
<212> TYPE: DNA
<213> ORGANISM: Artificial sequence
<220> FEATURE:
<223> OTHER INFORMATION: DENV3_LBv1

<400> SEQUENCE: 7
attggttatg gcgttta                                              17

<210> SEQ ID NO 8
<211> LENGTH: 30
<212> TYPE: DNA
<213> ORGANISM: Artificial sequence
<220> FEATURE:
<223> OTHER INFORMATION: DENV3_Qp

<400> SEQUENCE: 8
ctgaacggcc aaggaccaat gaaattggtt                                 30

<210> SEQ ID NO 9
<211> LENGTH: 13
<212> TYPE: DNA
<213> ORGANISM: Artificial sequence
<220> FEATURE:
<223> OTHER INFORMATION: DENV3_B3-m12

<400> SEQUENCE: 9
atctagccaa gac                                                   13

<210> SEQ ID NO 10
<211> LENGTH: 13
<212> TYPE: DNA
<213> ORGANISM: Artificial sequence
<220> FEATURE:
<223> OTHER INFORMATION: DENV3_B3-m13

<400> SEQUENCE: 10
ctagccaaga ctc                                                   13

<210> SEQ ID NO 11
<211> LENGTH: 13
<212> TYPE: DNA
<213> ORGANISM: Artificial sequence
<220> FEATURE:
<223> OTHER INFORMATION: DENV3_B3-m14

<400> SEQUENCE: 11
agccaagact cct                                                   13

<210> SEQ ID NO 12
<211> LENGTH: 13
<212> TYPE: DNA
<213> ORGANISM: Artificial sequence
<220> FEATURE:
<223> OTHER INFORMATION: DENV3_B3-m16

<400> SEQUENCE: 12
gacttcttga agg                                                   13
```

-continued

```
<210> SEQ ID NO 13
<211> LENGTH: 13
<212> TYPE: DNA
<213> ORGANISM: Artificial sequence
<220> FEATURE:
<223> OTHER INFORMATION: DENV3_B3-m18

<400> SEQUENCE: 13
tcttgaaggt tcc                                                          13

<210> SEQ ID NO 14
<211> LENGTH: 13
<212> TYPE: DNA
<213> ORGANISM: Artificial sequence
<220> FEATURE:
<223> OTHER INFORMATION: DENV3_B3-m19

<400> SEQUENCE: 14
ttgaaggttc ccc                                                          13

<210> SEQ ID NO 15
<211> LENGTH: 13
<212> TYPE: DNA
<213> ORGANISM: Artificial sequence
<220> FEATURE:
<223> OTHER INFORMATION: DENV3_B3-m20

<400> SEQUENCE: 15
ttcttgaagg ttc                                                          13

<210> SEQ ID NO 16
<211> LENGTH: 13
<212> TYPE: DNA
<213> ORGANISM: Artificial sequence
<220> FEATURE:
<223> OTHER INFORMATION: DENV3_B3-m21

<400> SEQUENCE: 16
cttgaaggtt ccc                                                          13

<210> SEQ ID NO 17
<211> LENGTH: 13
<212> TYPE: DNA
<213> ORGANISM: Artificial sequence
<220> FEATURE:
<223> OTHER INFORMATION: DENV3_B3-m23

<400> SEQUENCE: 17
aaggttcccc atc                                                          13

<210> SEQ ID NO 18
<211> LENGTH: 13
<212> TYPE: DNA
<213> ORGANISM: Artificial sequence
<220> FEATURE:
<223> OTHER INFORMATION: DENV3_B3-m25

<400> SEQUENCE: 18
ttgaaggttc ccc                                                          13

<210> SEQ ID NO 19
<211> LENGTH: 13
<212> TYPE: DNA
<213> ORGANISM: Artificial sequence
<220> FEATURE:
<223> OTHER INFORMATION: DENV3_B3-m26
```

-continued

```
<400> SEQUENCE: 19
gaaggttccc cat                                                       13

<210> SEQ ID NO 20
<211> LENGTH: 13
<212> TYPE: DNA
<213> ORGANISM: Artificial sequence
<220> FEATURE:
<223> OTHER INFORMATION: DENV3_B3-m27

<400> SEQUENCE: 20
aggttcccca tct                                                       13

<210> SEQ ID NO 21
<211> LENGTH: 13
<212> TYPE: DNA
<213> ORGANISM: Artificial sequence
<220> FEATURE:
<223> OTHER INFORMATION: DENV3_F4-1

<400> SEQUENCE: 21
gactcggaag ctt                                                       13

<210> SEQ ID NO 22
<211> LENGTH: 13
<212> TYPE: DNA
<213> ORGANISM: Artificial sequence
<220> FEATURE:
<223> OTHER INFORMATION: DENV3_F4-2

<400> SEQUENCE: 22
actcggaagc ttg                                                       13

<210> SEQ ID NO 23
<211> LENGTH: 14
<212> TYPE: DNA
<213> ORGANISM: Artificial sequence
<220> FEATURE:
<223> OTHER INFORMATION: DENV3_F4-3

<400> SEQUENCE: 23
gactcggaag cttg                                                      14

<210> SEQ ID NO 24
<211> LENGTH: 12
<212> TYPE: DNA
<213> ORGANISM: Artificial sequence
<220> FEATURE:
<223> OTHER INFORMATION: DENV3_F4-4

<400> SEQUENCE: 24
gactcggaag ct                                                        12

<210> SEQ ID NO 25
<211> LENGTH: 12
<212> TYPE: DNA
<213> ORGANISM: Artificial sequence
<220> FEATURE:
<223> OTHER INFORMATION: DENV3_F4-5

<400> SEQUENCE: 25
actcggaagc tt                                                        12

<210> SEQ ID NO 26
```

-continued

```
<211> LENGTH: 12
<212> TYPE: DNA
<213> ORGANISM: Artificial sequence
<220> FEATURE:
<223> OTHER INFORMATION: DENV3_F4-6

<400> SEQUENCE: 26
ctcggaagct tg                                                              12

<210> SEQ ID NO 27
<211> LENGTH: 1620
<212> TYPE: RNA
<213> ORGANISM: Artificial sequence
<220> FEATURE:
<223> OTHER INFORMATION: Hemagglutinin of Avian Influenza Virus (H5N1)

<400> SEQUENCE: 27
auggagaaaa uagugcuucu uuuugcaaua gucagucuug uuaaaaguga ucagauuugc      60
auugguuacc augcaaacaa cucgacagag cagguugaca caauaaugga aaagaacguu     120
acuguuacac augcccaaga cauacuggaa aagaaacaca acgggaagcu cugcgaucua     180
gauggaguga agccucuaau uuugagagau uguagcguag cuggauggcu ccucggaaac     240
ccaaugugug acgaauucau caaugugccg gaauggucuu acauagugga gaaggccaau     300
ccagucaaug accucuguua cccagggagau uucaaugacu augaagaauu gaaacaccua     360
uugagcagaa uaaaccauuu ugagaaaaau cagaucaucc ccaaaaguuc uugguccagu     420
caugaagccu cauuaggggu gagcucagca uguccauacc agggaaaguc ucccuuuuuc     480
agaaaugugg uauggcuuau caaaaagaac aguacauacc caacaauaaa gaggagcuac     540
aauaauacca accaagaaga ucuuuugguaa cuguggggga uucaccaucc uaaugaugcg     600
gcagagcaga caaagcucua ucaaaaccca accaccauaa uuuccguugg gacaucaaca     660
cuaaaccaga gauugguacc aagaauagcu acuagaucca aaguaaacgg gcaaagugga     720
aggauggagu cuucuggac aauuuuaaag ccgaaugaug caaucaacuu cgagaguaau     780
ggaaauuuca uugcuccaga auaugcauac aaaauuguca agaaggggga cucaacaauu     840
augaaaagug aauuggaaua ugguaacugc aacaccaagu gucaaacucc aaugggggcg     900
auaaacucua gcaugccauu ccacaauaua cacccucuca ccauggggga augccccaaa     960
uaugugaaau caaacagauu agccuugcg acgggcuca gaaauagccc ucaaagagag     1020
agaagaagaa aaaagagagg auuauuugga gcuauagcag guuuuauaga gggaggaugg     1080
cagggaaugg uagauggu guaugggugc caccauagca augagcaggg gaguggguac     1140
gcugcagaca aagaauccac ucaaaaggca auagauggag ucaccaauaa ggucaacucg     1200
aucauugaca aaaugaacac ucaguuuagg gccguuggaa gggaauuuaa aacuuagaa     1260 aggagaauag agaauuuaaa caagaagaug gaagacgggu uccuagaugu cuggacuuau     1320
aaugcugaac uucugguucu cauggaaaau gagagaacuc uagacuuuca ugacucaaau     1380
gucaagaacc uuuacgacaa gguccgacua cagcuuaggg auaaugcaaa ggagcugggu     1440
aacgguuguu ucgaguucua ucauaaaugu gauaaugaau guauggaaag uguaagaaau     1500
ggaacguaug acuacccgca guauucagaa gaagcgagac uaaaaagaga ggaaauaagu     1560
ggaguaaaau uggaaucaau aggaauuuac caaauacugu caauuuauuc uacaguggcg     1620

<210> SEQ ID NO 28
<211> LENGTH: 19
<212> TYPE: DNA
<213> ORGANISM: Artificial sequence
```

<220> FEATURE:
<223> OTHER INFORMATION: H5N1-F3v7

<400> SEQUENCE: 28
caattttaaa gccgaatga                                                        19

<210> SEQ ID NO 29
<211> LENGTH: 17
<212> TYPE: DNA
<213> ORGANISM: Artificial sequence
<220> FEATURE:
<223> OTHER INFORMATION: H5N1-B3

<400> SEQUENCE: 29
gtcgcaagga ctaatct                                                         17

<210> SEQ ID NO 30
<211> LENGTH: 47
<212> TYPE: DNA
<213> ORGANISM: Artificial sequence
<220> FEATURE:
<223> OTHER INFORMATION: H5N1-FIP

<400> SEQUENCE: 30
accatattcc aactcacttt tcataatttc attgcaccag aatatgc                         47

<210> SEQ ID NO 31
<211> LENGTH: 34
<212> TYPE: DNA
<213> ORGANISM: Artificial sequence
<220> FEATURE:
<223> OTHER INFORMATION: H5N1-BIP

<400> SEQUENCE: 31
caaactccaa tggggggcatg gtgagagggt gtat                                      34

<210> SEQ ID NO 32
<211> LENGTH: 20
<212> TYPE: DNA
<213> ORGANISM: Artificial sequence
<220> FEATURE:
<223> OTHER INFORMATION: H5N1-LF

<400> SEQUENCE: 32
gagtcccctt tcttgacaat                                                       20

<210> SEQ ID NO 33
<211> LENGTH: 19
<212> TYPE: DNA
<213> ORGANISM: Artificial sequence
<220> FEATURE:
<223> OTHER INFORMATION: H5N1-LB

<400> SEQUENCE: 33
gataaactct agtatgcca                                                        19

<210> SEQ ID NO 34
<211> LENGTH: 12
<212> TYPE: DNA
<213> ORGANISM: Artificial sequence
<220> FEATURE:
<223> OTHER INFORMATION: H5N1-F4v2

<400> SEQUENCE: 34
aaagtggaag ga                                                               12

```
<210> SEQ ID NO 35
<211> LENGTH: 12
<212> TYPE: DNA
<213> ORGANISM: Artificial sequence
<220> FEATURE:
<223> OTHER INFORMATION: H5N1-F4v6

<400> SEQUENCE: 35
gggcaaagtg ga                                                    12

<210> SEQ ID NO 36
<211> LENGTH: 12
<212> TYPE: DNA
<213> ORGANISM: Artificial sequence
<220> FEATURE:
<223> OTHER INFORMATION: H5N1-F4v7

<400> SEQUENCE: 36
cgggcaaagt gg                                                    12

<210> SEQ ID NO 37
<211> LENGTH: 13
<212> TYPE: DNA
<213> ORGANISM: Artificial sequence
<220> FEATURE:
<223> OTHER INFORMATION: H5N1-F4v17

<400> SEQUENCE: 37
gattggtacc aag                                                   13

<210> SEQ ID NO 38
<211> LENGTH: 12
<212> TYPE: DNA
<213> ORGANISM: Artificial sequence
<220> FEATURE:
<223> OTHER INFORMATION: H5N1-B4v1

<400> SEQUENCE: 38
tttctgagcc ca                                                    12

<210> SEQ ID NO 39
<211> LENGTH: 12
<212> TYPE: DNA
<213> ORGANISM: Artificial sequence
<220> FEATURE:
<223> OTHER INFORMATION: H5N1-B4v6

<400> SEQUENCE: 39
ggctatttct ga                                                    12

<210> SEQ ID NO 40
<211> LENGTH: 12
<212> TYPE: DNA
<213> ORGANISM: Artificial sequence
<220> FEATURE:
<223> OTHER INFORMATION: H5N1-B4v8

<400> SEQUENCE: 40
agggctattt ct                                                    12

<210> SEQ ID NO 41
<211> LENGTH: 1530
<212> TYPE: RNA
<213> ORGANISM: Artificial sequence
<220> FEATURE:
<223> OTHER INFORMATION: NS5 of ZIKV
```

-continued

<400> SEQUENCE: 41
guaauacgac ucacuauagg gaucaacaag guucguagca augcagcauu aggggcaaua      60
uuugaagagg aaaaagagug gaagacugca guggaagcug ugaacgaucc aagguucugg     120
gcucuagugg acaaggaaag agagcaccac cugagaggag agugccagag uuguguguac     180
aacaugaugg gaaaaagaga aaagaaacaa ggggaauuug gaaaggccaa gggcagccgc     240
gccaucuggu auauguggcu aggggcuaga uuucuagagu ucgaagcccu uggauucuug     300
aacgaggauc acuggauggg gagagagaac ucaggaggug uguugaagg gcugggauua     360 caaagacucg gauaugaccu agaagagaug agucguauac caggaggaag gauguaugca     420
gaugacacug cuggcuggga cacccgcauu agcagguuug aucuggagaa ugaagcucua     480
aucaccaacc aaauggagaa agggcacagg gccuuggcau uggccauaau caaguacaca     540
uaccaaaaca aagugguaaa gguccuuaga ccagcugaaa aagggaaaac aguuauggac     600
auuauuucga gacaagacca aagggggagc ggacaaguug ucacuuacgc ucuuaacaca     660
uuuaccaacc uaguggugca acucauucgg aauauggagg cugaggaagu ucuagagaug     720
caagacuugu ggcugcugcg gaggucagag aaagugacua acugguugca gagcaacgga     780
ugggauaggc ucaaacgaau ggcagucagu ggagaugauu gcguugugaa gccaauugau     840 gauagguug cacaugcccu cagguucuug aaugauaugg gaaaaguuag gaaggacaca     900
caagagugga aacccucaac uggaugggac aacugggaag aaguuccguu uugcucccac     960
cacuucaaca agcuccaucu caaggacggg aagguccauug ugguucccug ccgccaccaa    1020
gaugaacuga uuggccgggc ccgcgucucu ccaggggcgg gauggagcau ccgggagacu    1080
gcuugccuag caaaaucaua ugcgcaaaug uggcagcucc uuuauuucca cagaagggac    1140
cuccgacuga uggccaaugc cauuuguuca ucugugccag uugacugggu uccaacuggg    1200
agaacuaccu ggucaaucca uggaaaggga gaauggauga ccacugaaga caugcuugug    1260
guguggaaca gaguguggau ugaggagaac gaccacaugg aagacaagac cccaguuacg    1320
aaauggacag acauucccua uuugggaaaa agggaagacu uguggugugg aucucucaua    1380
gggcacagac cgcgcaccac cugggcugag aacauuaaaa acacagucaa cauggugcgc    1440
aggaucauag gugaugaaga aaaguacaug gacuaccuau ccacccaagu ucgcuacuug    1500
ggugaagaag ggcuacacc uggagugcug                                      1530

<210> SEQ ID NO 42
<211> LENGTH: 18
<212> TYPE: DNA
<213> ORGANISM: Artificial sequence
<220> FEATURE:
<223> OTHER INFORMATION: ZIKV F3

<400> SEQUENCE: 42
cagaagggac ctccgact                                                    18

<210> SEQ ID NO 43
<211> LENGTH: 20
<212> TYPE: DNA
<213> ORGANISM: Artificial sequence
<220> FEATURE:
<223> OTHER INFORMATION: ZIKV B3

<400> SEQUENCE: 43
cgtaactggg gtcttgtctt                                                  20

```
<210> SEQ ID NO 44
<211> LENGTH: 42
<212> TYPE: DNA
<213> ORGANISM: Artificial sequence
<220> FEATURE:
<223> OTHER INFORMATION: ZIKV FIP

<400> SEQUENCE: 44
ttgaccaggt agttctccca gtatggccaa tgccatttgt tc                42

<210> SEQ ID NO 45
<211> LENGTH: 42
<212> TYPE: DNA
<213> ORGANISM: Artificial sequence
<220> FEATURE:
<223> OTHER INFORMATION: ZIKV BIP

<400> SEQUENCE: 45
agggagaatg gatgaccact gactcctcaa tccacactct gt                42

<210> SEQ ID NO 46
<211> LENGTH: 18
<212> TYPE: DNA
<213> ORGANISM: Artificial sequence
<220> FEATURE:
<223> OTHER INFORMATION: ZIKV LF

<400> SEQUENCE: 46
cccagtcaac tggcacag                                           18

<210> SEQ ID NO 47
<211> LENGTH: 15
<212> TYPE: DNA
<213> ORGANISM: Artificial sequence
<220> FEATURE:
<223> OTHER INFORMATION: ZIKV LB

<400> SEQUENCE: 47
catgcttgtg gtgtg                                              15

<210> SEQ ID NO 48
<211> LENGTH: 29
<212> TYPE: DNA
<213> ORGANISM: Artificial sequence
<220> FEATURE:
<223> OTHER INFORMATION: ZIKV Qp

<400> SEQUENCE: 48
tggaacccag tcaactggca cagatgaac                               29

<210> SEQ ID NO 49
<211> LENGTH: 14
<212> TYPE: DNA
<213> ORGANISM: Artificial sequence
<220> FEATURE:
<223> OTHER INFORMATION: ZIKV_B4-3

<400> SEQUENCE: 49
tagggaatgt ctgt                                               14

<210> SEQ ID NO 50
<211> LENGTH: 12
<212> TYPE: DNA
<213> ORGANISM: Artificial sequence
<220> FEATURE:
<223> OTHER INFORMATION: ZIKV_B4-13
```

-continued

<400> SEQUENCE: 50
gaatgtctgt cc                                                          12

<210> SEQ ID NO 51
<211> LENGTH: 13
<212> TYPE: DNA
<213> ORGANISM: Artificial sequence
<220> FEATURE:
<223> OTHER INFORMATION: ZIKV_B4-14

<400> SEQUENCE: 51
tgtctgtcca ttt                                                         13

<210> SEQ ID NO 52
<211> LENGTH: 13
<212> TYPE: DNA
<213> ORGANISM: Artificial sequence
<220> FEATURE:
<223> OTHER INFORMATION: ZIKV_F4-2

<400> SEQUENCE: 52
ctcctttatt tcc                                                         13

<210> SEQ ID NO 53
<211> LENGTH: 17
<212> TYPE: DNA
<213> ORGANISM: Artificial sequence
<220> FEATURE:
<223> OTHER INFORMATION: ZIKV_F4-3

<400> SEQUENCE: 53
aaatcatatg cgcaaat                                                     17

<210> SEQ ID NO 54
<211> LENGTH: 1374
<212> TYPE: RNA
<213> ORGANISM: Artificial sequence
<220> FEATURE:
<223> OTHER INFORMATION: N gene of RABV

<400> SEQUENCE: 54
auggaugccg acaagauugu guucaaaguc aauaaucagg uggucucuuu gaagccugag      60
auuaucgugg aucaauauga guacaaguac ccugccauca aggauuugaa aaagccuugu     120 aucaccuag ggaaagccccc cgacuugaac aaagcauaca aaucaguuuu aucaggcaug     180
aaugccgcca aacuugaucc ggaugaugua ugcuccuacu uggcagcagc aaugcaguuc     240
uuugagggga cauguccgga agacuggacc agcuauggaa uccugauugc acgaaaagga     300
gacaggauca ccccaaacuc ucuaguggag auaaagcgua cugauguaga cgggaauugg     360
gcucugacag gaggcaugga auugacaagg accccacug ucucugaaca ugcaucuuua      420
gucggucuuc uccugagucu guacagguug agcaaaauau caggacagaa cacugguaac     480
uauaagacaa acauugcaga uaggauagag cagauuuucg agacagcacc uuuuguuaag     540
aucguggaac accauacccu aaugacaacu cacaagaugu gugcuaauug gaguacuaua     600
ccgaacuuca gauuuuuggc cggaaccuac gacauguuuu ucuacgggau ugagcaucug     660
uauucggcaa ucagaguggg cacagucguc accgcuuaug aagacugcuc aggacuggua     720
ucguuuacag ggGuucauaaa gcagaucaau cucaccgcaa gggaagcaau acuauauuuc     780
uuccacaaga acuuugagga agagauaaga agaaugggc agccagggca agagacagcu       840

```
guuccucacu cuuauuucau ccacuuccgu ucacuaggcu ugagugggaa gucuccuuau       900
ucaucgaaug cugucgguca uguguucaau cucauucacu uuguuggaug cuacaugggu       960
caagucagau cucuaaaugc gacgguuauu gcugcaugug ccccucauga gaugucuguu       1020 cuaggggggcu auuugggaga ggaauucuuc ggaaaaggga cauuugaaag aagguucuuc     1080
agagacgaga aagaacuuca agaauaugag gcggcugaac uaacaaagac cgacguggca      1140
cuggcagaug acggaaccgu caacucugau gacgaggacu auuucuccgg ugaaaccaga      1200
aguccagaag cugucuauac ucgaaucaug augaauggag gucgacugaa gagaucucau      1260
auacggagau augucucagu caguuccaau caucaagccc guccaaacuc auucgccgaa      1320
uuuuuaaaca agacguauuc gaaugacuca uaacccuaua gugagucgua uuac           1374
```

```
<210> SEQ ID NO 55
<211> LENGTH: 16
<212> TYPE: DNA
<213> ORGANISM: Artificial sequence
<220> FEATURE:
<223> OTHER INFORMATION: RABV1-F3

<400> SEQUENCE: 55
acatgtccgg aagact                                                      16

<210> SEQ ID NO 56
<211> LENGTH: 18
<212> TYPE: DNA
<213> ORGANISM: Artificial sequence
<220> FEATURE:
<223> OTHER INFORMATION: RABV1-B3

<400> SEQUENCE: 56
cagactcagg agaagacc                                                    18

<210> SEQ ID NO 57
<211> LENGTH: 37
<212> TYPE: DNA
<213> ORGANISM: Artificial sequence
<220> FEATURE:
<223> OTHER INFORMATION: RABV1-FIP

<400> SEQUENCE: 57
actagagagt ttggggtgag gaccagctat ggaatcc                               37

<210> SEQ ID NO 58
<211> LENGTH: 37
<212> TYPE: DNA
<213> ORGANISM: Artificial sequence
<220> FEATURE:
<223> OTHER INFORMATION: RABV1-BIP

<400> SEQUENCE: 58
acgggaattg ggctctgacc taaagatgca tgttcag                               37

<210> SEQ ID NO 59
<211> LENGTH: 22
<212> TYPE: DNA
<213> ORGANISM: Artificial sequence
<220> FEATURE:
<223> OTHER INFORMATION: RABV1-LB

<400> SEQUENCE: 59
ggcatggaat tgacaaggga cc                                               22
```

-continued

```
<210> SEQ ID NO 60
<211> LENGTH: 13
<212> TYPE: DNA
<213> ORGANISM: Artificial sequence
<220> FEATURE:
<223> OTHER INFORMATION: RABV1-F4v14

<400> SEQUENCE: 60
cagcagcaat gca                                                                              13

<210> SEQ ID NO 61
<211> LENGTH: 14
<212> TYPE: DNA
<213> ORGANISM: Artificial sequence
<220> FEATURE:
<223> OTHER INFORMATION: RABV1-B4v3

<400> SEQUENCE: 61
tattttgctc aacc                                                                             14

<210> SEQ ID NO 62
<211> LENGTH: 14
<212> TYPE: DNA
<213> ORGANISM: Artificial sequence
<220> FEATURE:
<223> OTHER INFORMATION: RABV1-B4v7

<400> SEQUENCE: 62
tgtcctgata tttt                                                                             14
```

METHOD FOR DETECTING SINGLE-STRANDED RNA VIRUS

RELATED PATENT APPLICATIONS

This application is based on and claims the benefit of priority from International Application No. PCT/JP2021/006907, filed on Feb. 24, 2021, which claims priority to Japanese Patent Application No. 2020-031780, filed on Feb. 27, 2020, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 12, 2022, is named "051723-0570954 SEQUENCE LISTING ST25.txt" and is 17.4 KB in size.

TECHNICAL FIELD

The present invention relates to a method for detecting a single-stranded RNA virus.

BACKGROUND ART

Viruses are organisms that parasitize cells and viruses cannot be cultured alone, and thus, a genetic diagnosis is mainly used as a method for identifying causative viruses in a short period of time in a diagnosis of a viral infectious disease. In a genetic diagnosis of a virus, a nucleic acid sequence unique to the target virus is amplified through a nucleic acid amplification reaction and detected.

A loop-mediated isothermal amplification (LAMP) method is known as a kind of nucleic acid amplification method (Patent Literature 1). In this method, two kinds of inner primers (an FIP primer and a BIP primer) and two kinds of outer primers (an F3 primer and a B3 primer) are designed based on six regions (F3, F2, F1, B1c, B2c, and B3c, or F3c, F2c, F1c, B1, B2, and B3) of a target nucleic acid, and the target nucleic acid is amplified at a constant temperature using these primers. In addition, in the LAMP method, it is known that the efficiency of an amplification reaction is improved using two kinds of loop primers (a loop primer F and a loop primer B) in addition to the above-described inner primers and outer primers (Patent Literature 2).

Viruses are classified into double-stranded DNA viruses, single-stranded RNA viruses, and the like, depending on the type of a nucleic acid of a genome. Single-stranded RNA viruses are classified into (+) strand (plus-strand) viruses in which genes are read in the direction from the 5' terminal to 3' terminal and (−) strand (minus-strand) viruses in which genes are read in the direction from the 3' terminal to 5' terminal via a complementary strand. When amplifying nucleic acids of RNA viruses, a reverse transcription reaction for synthesizing cDNA from template RNA using a reverse transcriptase is required at the start of an amplification reaction. The LAMP method combined with a reverse transcription reaction is called a reverse transcription loop-mediated isothermal amplification (RT-LAMP) method (for example, Patent Literature 3).

CITATION LIST

Patent Literature

[Patent Literature 1] PCT International Publication No. WO 00/28082

[Patent Literature 2] PCT International Publication No. WO 02/24902

[Patent Literature 3] PCT International Publication No. WO 2018/042598

SUMMARY OF INVENTION

Technical Problem

According to the LAMP methods disclosed in Patent Literature 1 to 3, viruses can be detected with relatively high sensitivity. However, since there are many diseases, among viral diseases, that cause severe symptoms, a method for more reliably detecting viruses that cause such diseases is needed. Therefore, an object of the present invention is to detect a single-stranded RNA virus with high sensitivity.

Solution to Problem

As a result of extensive studies, the present inventors have found that a single-stranded RNA virus can be detected with higher sensitivity by performing an RT-LAMP reaction using specific additional outer primers in addition to the conventional six kinds of primers, thus leading to realization of the present invention. According to the new findings of the present inventors, the sensitivity of detection is not improved when an outer primer that anneals to a region on 3' terminal side of a nucleic acid complementary to a target RNA of a single-stranded RNA virus is added, while the sensitivity of detection is improved when an outer primer that anneals to a region on 3' terminal side of a target RNA of a single-stranded RNA virus is added. The present invention relates to following [1] to [8].

[1] A method for detecting a single-stranded RNA virus in a sample, the method comprising:

bringing a primer set into contact with a sample to perform a reverse transcription loop-mediated isothermal amplification reaction, wherein the primer set is designed based on a nucleotide sequence of a target RNA of a single-stranded RNA virus and a nucleotide sequence of a nucleic acid complementary to the target RNA, wherein when the single-stranded RNA virus is a plus-strand single-stranded RNA virus, the target RNA comprises arbitrary regions F3, F2, F1, B1c, B2c, and B3c in this order in a direction from a 5' terminal to a 3' terminal, and the nucleic acid complementary to the target RNA comprises arbitrary regions F3c, F2c, F1c, B1, B2, and B3 in this order in a direction from a 3' terminal to a 5' terminal, wherein when the single-stranded RNA virus is a minus-strand single-stranded RNA virus, the target RNA comprises the arbitrary regions F3c, F2c, F1c, B1, B2, and B3 in this order in a direction from the 3' terminal to 5' terminal, and the nucleic acid complementary to the target RNA comprises the arbitrary regions F3, F2, F1, B1c, B2c, and B3c in this order in a direction from the 5' terminal to 3' terminal, wherein the primer set comprises following (i) to (v):

(i) an FIP primer having the same nucleotide sequence as the region F1c at a 5' terminal and having the same nucleotide sequence as the region F2 at a 3' terminal;

(ii) a BIP primer having the same nucleotide sequence as the region B1c at a 5' terminal and having the same nucleotide sequence as the region B2 at a 3' terminal;

(iii) an F3 primer which is an outer primer having the same nucleotide sequence as the region F3;

(iv) a B3 primer which is an outer primer having the same nucleotide sequence as the region B3; and (v) one or more additional outer primers, each additional outer primer having the same nucleotide sequence as an arbitrary region present on 5' terminal side from the region B3 or the region F3 in the nucleic acid complementary to the target RNA, and wherein uracil that may be present in the nucleotide sequences of the FIP primer, the BIP primer, the F3 primer, the B3 primer, and the one or more additional outer primers may be substituted with thymine.

[2] A method for detecting a plus-strand single-stranded RNA virus in a sample, the method comprising:

bringing a primer set into contact with a sample to perform a reverse transcription loop-mediated isothermal amplification reaction, wherein the primer set is designed based on a nucleotide sequence of a target RNA comprising arbitrary regions F3, F2, F1, B1c, B2c, and B3c in this order in a direction from a 5' terminal to a 3' terminal and a nucleotide sequence of a nucleic acid complementary to the target RNA comprising arbitrary regions F3c, F2c, F1c, B1, B2, and B3 in this order in a direction from a 3' terminal to a 5' terminal, and comprises following (i) to (v):

(i) an FIP primer having the same nucleotide sequence as the region F1c at a 5' terminal and having the same nucleotide sequence as the region F2 at a 3' terminal;

(ii) a BIP primer having the same nucleotide sequence as the region B1c at a 5' terminal and having the same nucleotide sequence as the region B2 at a 3' terminal;

(iii) an F3 primer which is an outer primer having the same nucleotide sequence as the region F3;

(iv) a B3 primer which is an outer primer having the same nucleotide sequence as the region B3; and (v) one or more additional outer primers, each additional outer primer having the same nucleotide sequence as an arbitrary region present on 5' terminal side from the region B3 in the nucleic acid complementary to the target RNA, and wherein uracil that may be present in the nucleotide sequences of the FIP primer, the BIP primer, the F3 primer, the B3 primer, and the one or more additional outer primers may be substituted with thymine.

[3] A method for detecting a minus-strand single-stranded RNA virus in a sample, the method comprising:

bringing a primer set into contact with a sample to perform a reverse transcription loop-mediated isothermal amplification reaction, wherein the primer set is designed based on a nucleotide sequence of a target RNA comprising arbitrary regions F3c, F2c, F1c, B1, B2, and B3 in this order in a direction from a 3' terminal to a 5' terminal and a nucleotide sequence of a nucleic acid complementary to the target RNA comprising arbitrary regions F3, F2, F1, B1c, B2c, and B3c in this order in a direction from the 5' terminal to 3' terminal, and comprises following (i) to (v):

(i) an FIP primer having the same nucleotide sequence as the region F1c at a 5' terminal and having the same nucleotide sequence as the region F2 at a 3' terminal;

(ii) a BIP primer having the same nucleotide sequence as the region B1c at a 5' terminal and having the same nucleotide sequence as the region B2 at a 3' terminal;

(iii) an F3 primer which is an outer primer having the same nucleotide sequence as the region F3;

(iv) a B3 primer which is an outer primer having the same nucleotide sequence as the region B3; and (v) one or more additional outer primers, each additional outer primer having the same nucleotide sequence as an arbitrary region present on 5' terminal side from the region F3 in the nucleic acid complementary to the target RNA, and wherein uracil that may be present in the nucleotide sequences of the FIP primer, the BIP primer, the F3 primer, the B3 primer, and the one or more additional outer primers may be substituted with thymine.

[4] The method according to any one of [1] to [3], wherein the primer set further comprises:

(vi) a loop primer F having the same nucleotide sequence as an arbitrary region between the region F1c and the region F2c; and (vii) a loop primer B having the same nucleotide sequence as an arbitrary region between the region B1c and the region B2c, and wherein uracil that may be present in the nucleotide sequences of the loop primer F and the loop primer B may be substituted with thymine.

[5] The method according to any one of [1] to [4], wherein a melting temperature of the one or more additional outer primers of (v) is 30° C. to 55° C.

[6] The method according to any one of [1] to [5], wherein the primer set comprises the one additional outer primer of (v).

[7] The method according to any one of [1] to [6], the method further comprising: detecting an amplification product of the reverse transcription loop-mediated isothermal amplification reaction.

[8] A kit for detecting a single-stranded RNA virus, the kit comprising:

a primer set, wherein the primer set is designed based on a nucleotide sequence of a target RNA of a single-stranded RNA virus and a nucleotide sequence of a nucleic acid complementary to the target RNA, wherein when the single-stranded RNA virus is a plus-strand single-stranded RNA virus, the target RNA comprises arbitrary regions F3, F2, F1, B1c, B2c, and B3c in this order in a direction from a 5' terminal to a 3' terminal, and the nucleic acid complementary to the target RNA comprises arbitrary regions F3c, F2c, F1c, B1, B2, and B3 in this order in a direction from a 3' terminal to a 5' terminal, wherein when the single-stranded RNA virus is a minus-strand single-stranded RNA virus, the target RNA comprises the arbitrary regions F3c, F2c, F1c, B1, B2, and B3 in this order in the direction from the 3' terminal to 5' terminal, and the nucleic acid complementary to the target RNA comprises the arbitrary regions F3, F2, F1, B1c, B2c, and B3c in this order in the direction from the 5' terminal to 3' terminal, wherein the primer set comprises following (i) to (v):

(i) an FIP primer having the same nucleotide sequence as the region F1c at a 5' terminal and having the same nucleotide sequence as the region F2 at a 3' terminal;

(ii) a BIP primer having the same nucleotide sequence as the region B1c at a 5' terminal and having the same nucleotide sequence as the region B2 at a 3' terminal;

(iii) an F3 primer which is an outer primer having the same nucleotide sequence as the region F3;

(iv) a B3 primer which is an outer primer having the same nucleotide sequence as the region B3; and (v) one or more additional outer primers, each additional outer primer having the same nucleotide sequence as an arbitrary region present on 5' terminal side from the region B3 or the region F3 in the nucleic acid complementary to the target RNA, and wherein uracil that may be present in the nucleotide sequences of the FIP primer, the BIP primer, the F3 primer, the B3 primer, and the one or more additional outer primers may be substituted with thymine.

Advantageous Effects of Invention

According to the present invention, a single-stranded RNA virus can be detected with high sensitivity.

DESCRIPTION OF EMBODIMENTS

Figure 1:
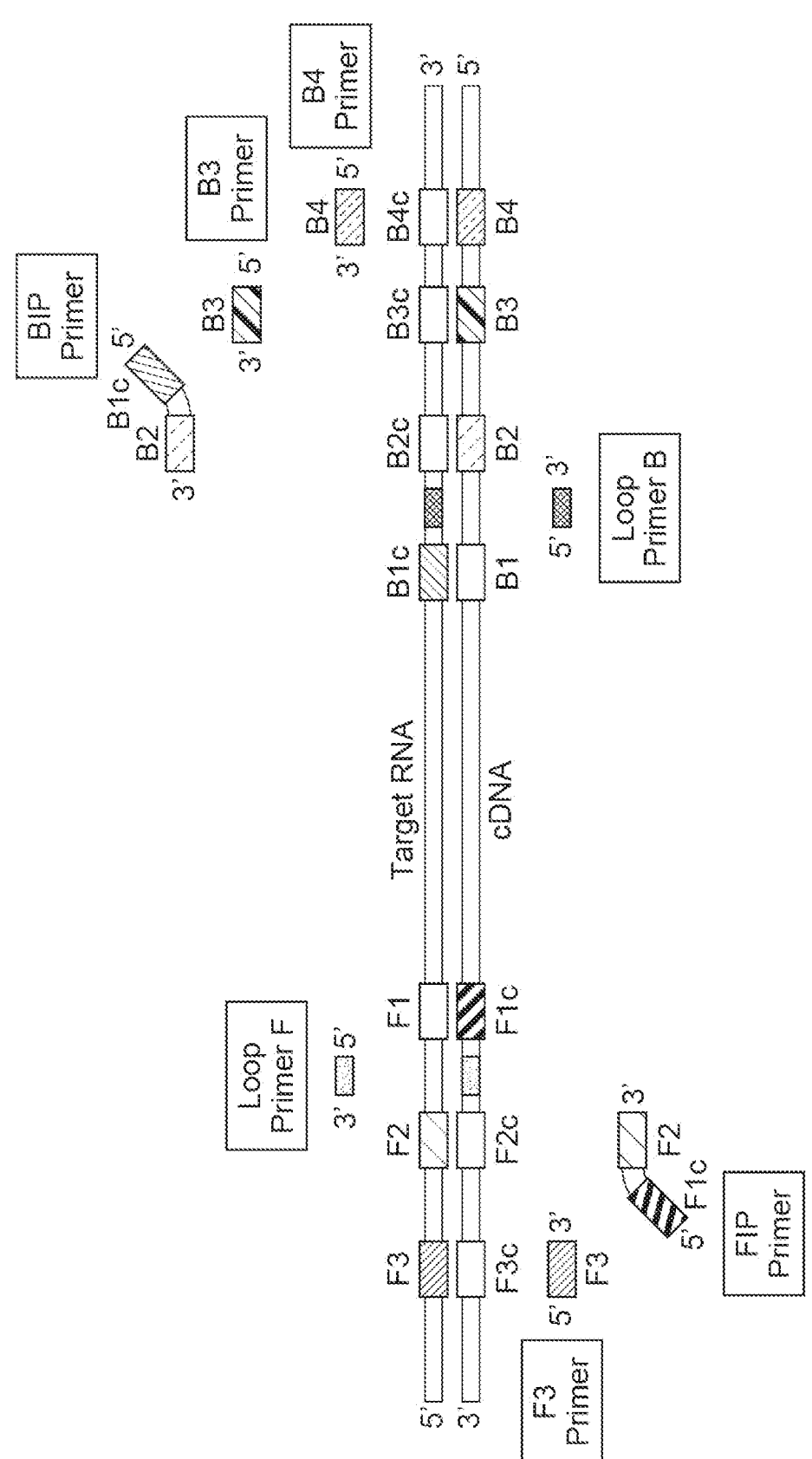
FIG. 1 shows regions F3, F2, F1, B1c, B2c, B3c, and B4c in a target RNA of a (+)ssRNA virus, regions F3c, F2c, F1c, B1, B2, B3, and B4 in cDNA complementary to the target RNA, and a primer set (an FIP primer, a BIP primer, an F3 primer, a B3 primer, a B4 primer, a loop primer F, and a loop primer B) designed based on these nucleotide sequences.

A method for detecting a single-stranded RNA virus in a sample according to an aspect of the present invention is a method which involves detecting nucleic acid amplification through an RT-LAMP method to detect a single-stranded RNA virus in a sample, and is characterized by the use of one or more additional outer primers that anneal to a region on a 3' terminal side of a target RNA in addition to the conventional primers (that is, an FIP primer, a BIP primer, an F3 primer, a B3 primer, and optionally an arbitrary loop primer F and a loop primer B) as a primer set. More specifically, the method for detecting a single-stranded RNA virus in a sample according to one aspect of the present invention comprises bringing a primer set into contact with a sample to perform an RT-LAMP reaction, wherein the primer set comprises an FIP primer, a BIP primer, an F3 primer, a B3 primer, and one or more additional outer primers to be described below, and optionally a loop primer F and a loop primer B.

A single-stranded RNA virus to be detected may be a plus-strand single-stranded RNA ((+)ssRNA) virus or may be a minus-strand single-stranded RNA ((−)ssRNA) virus. The (+)ssRNA virus is not particularly limited, and may be, for example, dengue viruses such as dengue virus type 3 (DENV3), rubella virus, hepatitis C virus, norovirus, chikungunya virus, zika virus (ZIKV), coronaviruses, human immunodeficiency virus (HIV), or hepatitis A virus. The (−)ssRNA virus is not particularly limited, and may be, for example, influenza viruses, Sendai virus, measles virus, human metapneumovirus, or rabies virus (RABV).

The sample may be a sample collected from a subject suspected of being infected with a single-stranded RNA virus, and may be, for example, sputum, body fluids, feces, or tissue. The body fluids may be, for example, nasal mucus, saliva, blood, serum, plasma, cerebrospinal fluid, urine, semen, or amniotic fluid. In addition, the sample may be bronchoalveolar lavage fluid, nasal suction fluid, nasal lavage fluid, a nasal swab, a pharyngeal swab, or mouthwash. Alternatively, the sample may be cells used in an experiment such as an infection experiment, or a culture liquid thereof. The sample may also be the above samples that have been subjected to pretreatment such as separation, extraction, concentration, and purification.

Target RNA may be the whole or a part of single-stranded RNA possessed by a single-stranded RNA virus. The length of the target RNA is not particularly limited, and may be, for example, 200 to 30,000 bases, 200 to 1,000 bases, or 200 to 550 bases.

The terms "FIP primer", "BIP primer", "F3 primer", "B3 primer", "loop primer F", and "loop primer B" in the present specification are synonymous with these terms in the conventional LAMP method, and are understood by those skilled in the art. In other words, primers other than the additional outer primers to be described below can be designed by those skilled in the art as appropriate, based on the disclosure of known literature.

Figure 2:
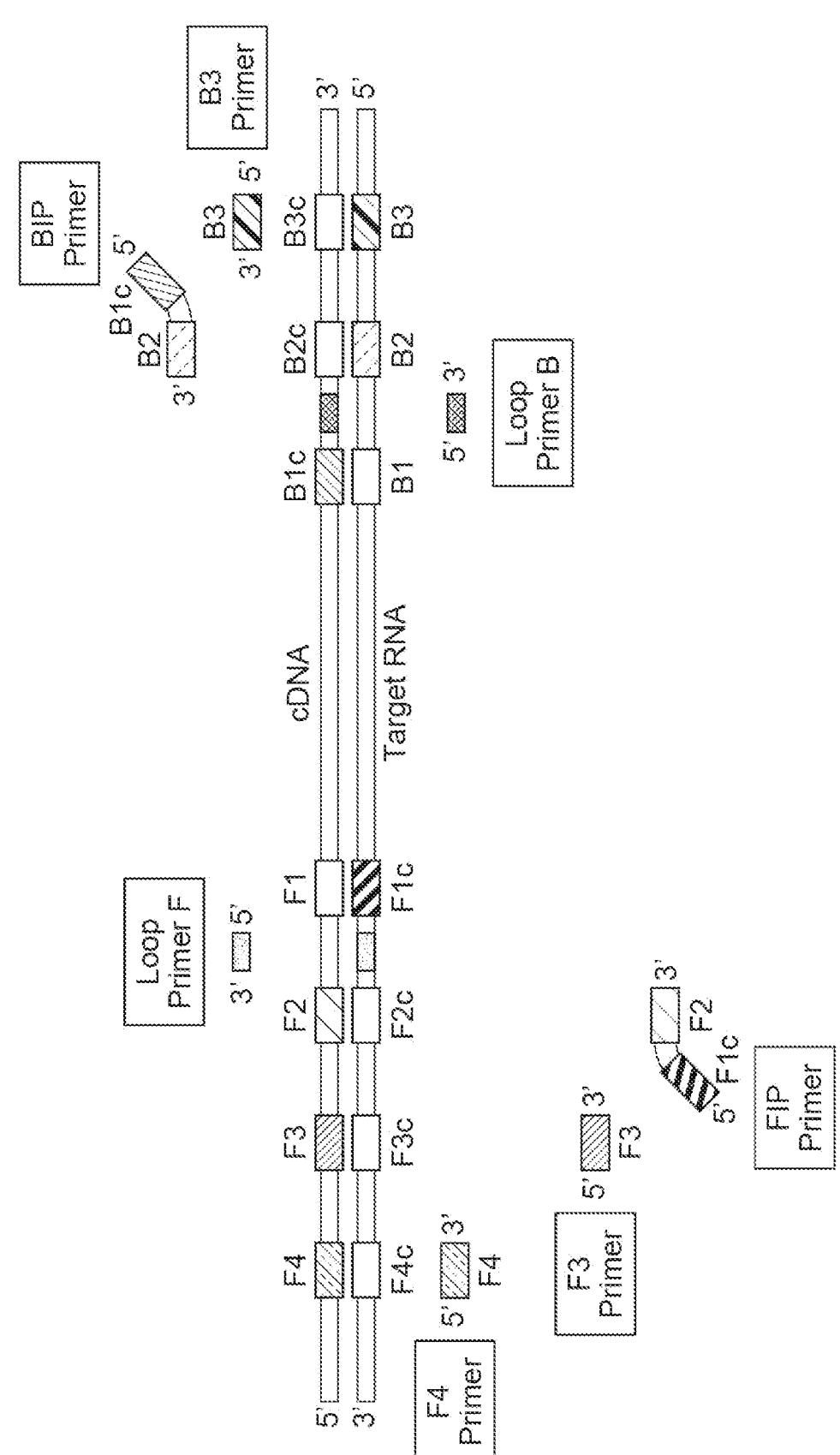
FIG. 2 shows regions F4c, F3c, F2c, F1c, B1, B2, and B3 in a target RNA of a (−)ssRNA virus, regions F4, F3, F2, F1, B1c, B2c, and B3c in cDNA complementary to the target RNA, and a primer set (an FIP primer, a BIP primer, an F3 primer, a B3 primer, an F4 primer, a loop primer F, and a loop primer B) designed based on these nucleotide sequences.

Hereinafter, a primer set of the method according to the present aspect will be described with reference to FIGS. 1 and 2. The primer set is designed based on a nucleotide sequence of target RNA of a single-stranded RNA virus and a nucleotide sequence of a nucleic acid complementary to the target RNA. Of the target RNA and the nucleic acid complementary to the target RNA, in a strand having a nucleotide sequence that can directly serve as a template for protein synthesis, arbitrary regions that serve as a base for a primer design are called regions F4, F3, F2, F1, B1c, B2c, B3c, and B4c in order from the 5' terminal side to 3' terminal side. On the other hand, in a strand having a nucleotide sequence that cannot directly serve as a template for protein synthesis, arbitrary regions that serve as a base for a primer design are called regions F4c, F3c, F2c, F1c, B1, B2, B3, and B4 in order from 3' terminal side to 5' terminal side. The nucleotide sequences of the regions F4, F3, F2, F1, B1c, B2c, B3c, and B4c are respectively complementary to the regions F4c, F3c, F2c, F1c, B1, B2, B3, and B4. Accordingly, when a single-stranded RNA virus to be detected is a (+)ssRNA virus, the regions F3, F2, F1, B1c, B2c, B3c, and B4c are arbitrary regions present in this order in the direction from the 5' terminal to 3' terminal of a target RNA, and the regions F3c, F2c, F1c, B1, B2, B3, and B4 are arbitrary regions present in this order in the direction from 3' terminal to 5' terminal of a nucleic acid complementary to the target RNA, as shown in FIG. 1. On the other hand, when a single-stranded RNA virus to be detected is a (−)ssRNA virus, the regions F4, F3, F2, F1, B1c, B2c, and B3c are arbitrary regions present in this order in the direction from the 5' terminal to 3' terminal of a nucleic acid complementary to a target RNA, and the regions F4c, F3c, F2c, F1c, B1, B2, and B3 are arbitrary regions present in this order in the direction from 3' terminal to 5' terminal of the target RNA, as shown in FIG. 2. Although cDNA is shown in FIGS. 1 and 2 as a nucleic acid complementary to a target RNA, a nucleic acid complementary to a target RNA is not limited to DNA, and may be RNA.

In the present specification, the term "complementary" does not necessarily mean being completely complementary. For example, the scope of a "nucleotide sequence complementary to a certain nucleotide sequence" encompasses a nucleotide sequence of a nucleic acid that hybridizes with a nucleic acid having the certain nucleotide sequence under stringent conditions. The stringent conditions are not particularly limited but may be, for example, 50% formamide, 5×SSC (150 mL NaCl and 15 mM trisodium citrate), 50 mM sodium phosphate (pH 7.6), a 5×Denhardt's solution, and 10% dextran sulfate.

In the present specification, the term "same" does not necessarily mean being exactly the same. For example, the scope of the "same nucleotide sequence as a certain nucleotide sequence" encompasses a nucleotide sequence complementary to a nucleotide sequence complementary to the certain nucleotide sequence.

As is understood by those skilled in the art, the FIP primer, which is an inner primer, has the same nucleotide sequence as the region F1c at 5' terminal and the same nucleotide sequence as the region F2 at 3' terminal. However, when there is uracil in the region F1c or the region F2, the corresponding uracil in the FIP primer may be substituted with thymine. There may or may not be one or more nucleotides serving as a linker between the same nucleotide sequence as that of the region F1c and the same nucleotide sequence as that of the region F2. The nucleotides serving as a linker may be 1 to 500 bases, 1 to 100 bases, or 10 to 70 bases.

As is understood by those skilled in the art, the BIP primer, which is an inner primer, has the same nucleotide sequence as the region B1c at 5' terminal and the same nucleotide sequence as the region B2 at 3' terminal. However, when there is uracil in the region B1c or the region B2, the corresponding uracil in the BIP primer may be substituted with thymine.

As is understood by those skilled in the art, the F3 primer, which is an outer primer, has the same nucleotide sequence as the region F3. However, when there is uracil in the region F3, the corresponding uracil in the F3 primer may be substituted with thymine.

As is understood by those skilled in the art, the B3 primer, which is an outer primer, has the same nucleotide sequence as the region B3. However, when there is uracil in the region B3, the corresponding uracil in the B3 primer may be substituted with thymine.

As is understood by those skilled in the art, the loop primer F has the same nucleotide sequence as an arbitrary region between the region F1c and the region F2c. However, when there is uracil in the arbitrary region between the region F1c and the region F2c, the corresponding uracil in the loop primer F may be substituted with thymine.

As is understood by those skilled in the art, the loop primer B has the same nucleotide sequence as an arbitrary region between the region B1c and the region B2c. However, when there is uracil in the arbitrary region between the region B1c and the region B2c, the corresponding uracil in the loop primer B may be substituted with thymine.

As described above, those skilled in the art can appropriately design the FIP, BIP, F3, and B3 primers, the loop primer F, and the loop primer B suitable for amplification of the target RNA. In other words, those skilled in the art can appropriately select regions suitable as the regions F3, F2, F1, B1c, B2c, and B3c in the target RNA. The length (number of bases) of each region may be, for example, 5 bases or more, 10 bases or more, 5 to 200 bases, 10 to 25 bases, 10 to 20 bases, or 17 to 25 bases. The melting temperature (Tm) of each region may be, for example, 55° C. to 65° C., 60° C. to 65° C., or 55° C. to 60° C. The Tm value in the present specification is a value calculated by a nearest-neighbor method (In a reaction solution, sodium ion concentration: 50 mM, magnesium ion concentration: 4 mM, and oligonucleic acid concentration: 0.1 μM). The CG content in each region may be, for example, 40% to 60%, 40% to 50%, or 50% to 60%. The free energy change (dG) of 6 bases from the 5' terminal of the regions F1c and B1c may be −4 kcal/mol or less. The dG of 6 bases from 3' terminal of the regions F2, B2, F3, B3 and the region serving as a base for designing loop primer F or B may also be −4 kcal/mol or less. Each primer preferably has a nucleotide sequence that does not form an extreme secondary structure. In addition, from the viewpoint of preventing formation of primer dimers, 3' terminal of each primer preferably does not have a nucleotide sequence complementary to its own 3' terminal or 3' terminal of other primers.

The distance from the 5' terminal of the region F2 to 3' terminal of the region B2c may be, for example, 120 to 180 bases. The distance between the region F2 and the region F3, and the distance between the region B2c and the region B3c may be, for example, 0 to 20 bases. The distance from the 5' terminal of the region F2 to 5' terminal of the region F1, and the distance from the 5' terminal of the region B2 to 5' terminal of the region B1 may be, for example, 40 to 60 bases. The distance from the region F1 to the region B1c is not particularly limited, and 3' terminal of the region F1 and 5' terminal of the region B1c may be directly connected to each other.

When a single-stranded RNA virus to be detected is a (+)ssRNA virus, the above-described additional outer primer has the same nucleotide sequence as an arbitrary region present on 5' terminal side from the region B3 in the nucleic acid complementary to the target RNA. However, when there is uracil in that region, the corresponding uracil in the above-described additional outer primer may be substituted with thymine. In FIG. 1, the B4 primer is the above-described additional outer primer, and the B4 primer has the same nucleotide sequence as an arbitrary region B4 present on 5' terminal side from the region B3 in cDNA complementary to the target RNA.

When a single-stranded RNA virus to be detected is a (−)ssRNA virus, the above-described additional outer primer has the same nucleotide sequence as an arbitrary region present on 5' terminal side from the region F3 in the nucleic acid complementary to the target RNA. However, when there is uracil in that region, the corresponding uracil in the above-described additional outer primer may be substituted with thymine. In FIG. 2, the F4 primer is the above-described additional outer primer, and the F4 primer has the same nucleotide sequence as an arbitrary region F4 present on 5' terminal side from the region F3 in cDNA complementary to the target RNA.

The Tm value of the above-described additional outer primer may be, for example, 30° C. to 55° C., 33° C. to 50° C., or 35° C. to 45° C. The length of the additional outer primer is not particularly limited, and may be, for example, 10 to 18 bases, 11 to 16 bases, or 12 to 14 bases. The CG content of the additional outer primer may be, for example, 30% to 70%, 34% to 65%, or 38% to 54%. The dG of 6 bases from the 3' terminal of the additional outer primer may be −4 kcal/mol or less. The additional outer primer preferably has a nucleotide sequence that does not form an extreme secondary structure. In addition, from the viewpoint of preventing formation of primer dimers, 3' terminal of the additional outer primer preferably does not have a nucleotide sequence complementary to its own 3' terminal or 3' terminal of other primers.

The location of the above-described arbitrary region (that is, the region B4 in FIG. 1 and the region F4 in FIG. 2) that serves as a base for designing the above-described additional outer primer is not particularly limited as long as a part or the whole of the region is present on 5' terminal side from the region B3 (in the case of the (+)ssRNA virus) or the region F3 (in the case of the (−)ssRNA virus) in the nucleic acid complementary to the target RNA, and the distance from the region B3 or the region F3 is not particularly limited. The distance from the 5' terminal of the region B3 or the region F3 to 3' terminal of the above-described arbitrary region that serves as a base for designing the additional outer primer may be, for example, −4 to 50 bases, −3 to 35 bases, or −2 to 21 bases. Here, when the above-described arbitrary region that serves as a base for designing the outer primer partially overlaps with the region B3 or the region F3, the distance from the 5' terminal of the region B3 or the region F3 to 3' terminal of the above-described arbitrary region that serves as a base for designing the additional outer primer is shown in a negative value.

Although the above-described additional outer primer is only the B4 primer in FIG. 1 and only the F4 primer in FIG. 2, the number of additional outer primers is not limited, and a plurality of additional outer primers may be included in a primer set. From the viewpoint of achieving higher detection sensitivity, the number of additional outer primers included in a primer set is preferably one.

Known reagents such as a reverse transcriptase, a DNA polymerase, and deoxynucleoside triphosphates (dNTPs: dATP, dTTP, dCTP, and dGTP) for performing an RT-LAMP reaction may be brought into contact with a sample together with the above-described primer set. DNA polymerase is not particularly limited as long as it is a template-dependent nucleic acid synthase with a strand substitution activity, and may be, for example, a Bst DNA polymerase (large fragment), a Bca(exo-) DNA polymerase, a Csa DNA polymerase, Klenow fragment of *Escherichia coli* DNA polymerase I, or a combination thereof.

Reverse transcriptase is not particularly limited as long as it is an enzyme with an activity of synthesizing cDNA using RNA as a template, and may be, for example, a natural or recombinant reverse transcriptase derived from a natural or recombinant avian myeloblastosis virus (AMV), murine leukemia virus (MMLV), or human immunodeficiency virus (HIV). Examples of a reverse transcriptase derived from MMLV include SuperScript (registered trademark) II reverse transcriptase, SuperScript III reverse transcriptase, and SuperScript IV reverse transcriptase (all are manufactured by Thermo Fisher Scientific Inc.), and ReverTra Ace (registered trademark) (manufactured by TOYOBO Co., LTD.). Examples of a reverse transcriptase derived from AMV include ThermoScript (registered trademark) reverse transcriptase (manufactured by Thermo Fisher Scientific Inc.). Other specific examples of a reverse transcriptase include OmniScript (registered trademark) reverse transcriptase and Sensiscript (registered trademark) reverse transcriptase (both are manufactured by QIAGEN N.V.). When using an enzyme, such as a BCa(exo-) DNA polymerase, having both a reverse transcriptase activity and a DNA polymerase activity as a DNA polymerase, a separate reverse transcriptase may not be necessarily used.

Examples of other known reagents for performing an RT-LAMP reaction include a buffer solution or a salt that provides suitable conditions for enzymatic reactions, and a protective agent that stabilizes a template or an enzyme such as dithiothreitol (DTT).

A labeling probe or a fluorescent intercalator for detecting amplification products of an RT-LAMP reaction may be brought into contact with a sample together with the above-described primer set. The labeling probe may be, for example, a fluorescence labeling probe, and the fluorescence labeling probe may be, for example, a fluorescence quenching probe to be described below.

The step of bringing a primer set into contact with a sample to perform an RT-LAMP reaction may be performed, for example, by incubating a reaction solution containing the sample and the primer set.

The reaction solution may contain the above-described known reagents for performing an RT-LAMP reaction and the above-described labeling probe or fluorescent intercalator. The incubation time (that is, the reaction time of the RT-LAMP reaction) is usually 60 minutes or less, although it depends on the target RNA and the primer set. The incubation temperature (that is, the reaction temperature of the RT-LAMP reaction) is usually 65° C. or less.

The concentration of each inner primer in a reaction solution may be, for example, 0.8 to 2.4 µM. The concentration of each outer primer in a reaction solution may be, for example, 0.1 to 0.3 µM. The concentration of each loop primer in a reaction solution may be, for example, 0.4 to 1.2 µM. The concentration of an FIP primer may be, for example, 8 times or more of the concentration of an F3 primer and/or 1 to 4 times of the concentration of a loop primer F. The concentration of a BIP primer may be, for example, 8 times or more of the concentration of a B3 primer and/or 1 to 4 times of the concentration of a loop primer B.

In one embodiment, the method for detecting a single-stranded RNA virus in a sample may further comprise detecting an amplification product of an RT-LAMP reaction. When an amplification product of an RT-LAMP reaction is detected, it can be determined that there is a single-stranded RNA virus in the sample. The detection of an amplification product may be performed after the completion of the RT-LAMP reaction or may be performed in real time during the reaction.

The method for detecting an amplification product is not particularly limited, and known technology may be used. An amplification product may be detected, for example, by using a labeling probe, by using a fluorescent intercalator, or by performing electrophoresis on the reaction solution. Alternatively, in a case where magnesium ions are contained in the reaction solution, an amplification product may be detected by measuring the turbidity of the reaction solution. Magnesium ions react with pyrophosphate ions, which are by-products of nucleic acid synthesis, to produce white magnesium pyrophosphate.

As the labeling probe, a fluorescence labeling probe such as a fluorescence quenching probe (Quenching Probe: QProbe (registered trademark)), for example, may be used. Since fluorescence emitted from a fluorescence quenching probe is quenched when the probe is hybridized with a target nucleic acid, the amplification product can be quantified or detected by measuring the decrease in fluorescence. Examples of fluorescent labels that may be used in a fluorescence quenching probe include BODIPY (registered trademark), BODIPY-FL, carboxyrhodamine 6G (CR6G), carboxytetramethylrhodamine (TAMRA), Pacific Blue (registered trademark), and fluorescein-4-isothiocyanate (FITC).

As the fluorescent intercalator, known fluorescent intercalator such as SYTO (registered trademark) 63 Red Fluorescent Nucleic Acid Stain (manufactured by Thermo Fisher Scientific Inc.), for example, may be used.

Another aspect of the present invention is a kit for detecting a single-stranded RNA virus comprising the above-described primer set. The kit may further comprise the above-described known reagents such as a reverse transcriptase, a DNA polymerase, dNTPs, a buffer solution, a salt, and a protective agent for performing an RT-LAMP reaction. In addition, the kit may further comprise the above-described labeling probe or fluorescent intercalator.

EXAMPLES

[Test Example 1] Detection of (+)ssRNA Virus (DENV3)

Reference Example 1

25 μL of a reaction solution having following composition was prepared in a 0.2 mL reagent tube:
20 mM Tricine (pH 8.6),
30 mM KCl,
8 mM MgSO$_4$,
1.4 mM dNTPs,
0.5% Tween 20,
1.6 mM DTT,
1.6 μM FIP Primer and BIP Primer,
0.2 μM F3 Primer and B3 Primer,
0.8 μM Loop Primer F and Loop Primer B,
AMV Reverse Transcriptase 1.0 U (20 U/μL, Manufactured by Roche),
Bst DNA polymerase 22.8 U (Manufactured by New England Biolabs),
RNase Inhibitor (40 U/μL, Manufactured by Promega) 1 μL,
Template RNA (100 copies) 5 μL,
PPase 20 mU (Manufactured by New England Biolabs), and
0.04 UM QProbe (Registered Trademark)
As an FIP primer, a BIP primer, an F3 primer, a B3 primer, a Loop primer F, a loop primer B, and QProbe, DENV3_FIPv4, DENV3_BIPv6, DENV3_F3, DENV3_B3a, DENV3_LF, DENV3_LBv1, and DENV3_Qp shown in Table 1 were respectively used. Template RNA (SEQ ID NO: 1) was prepared by integrating cDNA prepared by RT-PCR from DENV3 Capsid gene into a plasmid, and transcribing and purifying RNA from the plasmid DNA. Script Max (registered trademark) Thermo T7 Transcription Kit (manufactured by TOYOBO Co., LTD., Code Number: TSK-101) was used for the transcription, and RNeasy (registered trademark) Mini Kit (manufactured by QIAGEN N.V., Catalog Number: No. 74104) was used for RNA purification. The 5' terminal of QProbe was labeled with BODIPY, and 3' terminal thereof was phosphorylated.

TABLE 1

| Primer or probe | SEQ ID NO. | Sequence (from 5' to 3') | Tm (° C.) |
|---|---|---|---|
| DENV3_F3 | 2 | CTTAACGTAGTGCTGACAGTT | 57.41 |
| DENV3_B3a | 3 | CTGCTGTTGGTGGAATGG | 57.50 |
| DENV3_FIPv4 | 4 | TCTCACGCGTTTCAGCATATTG-A GAGAGCAGATCTCTGATGAACAACC | 76.13 |

TABLE 1-continued

| Primer or probe | SEQ ID NO. | Sequence (from 5' to 3') | Tm (° C.) |
|---|---|---|---|
| DENV3_BIPv6 | 5 | TGGCGAAGAGATTCTCAAGAGGA-CTAGAAATCTGAGGAAAGC | 73.41 |
| DENV3_LF | 6 | TTCCCGTCTTTTTCCGTTGG | 60.29 |
| DENV3_LBv1 | 7 | ATTGGTTATGGCGTTTA | 49.49 |
| DENV3_Qp | 8 | bodipy-CTGAACGGCCAAGGACC AATGAAATTGGTT-PHO | 69.84 |

An RT-LAMP reaction was performed (N=6) at 63° C. for 60 minutes using a real time quantitative PCR system LightCycler (registered trademark) 96 (manufactured by Roche). In addition, the same RT-LAMP reaction was performed (N=6) with the concentration of the B3 primer increased 2 to 4 times. An amplification product of the RT-LAMP reaction was detected by detecting quenching of QProbe in real time. The results are shown in Table 2. In addition, for reference, detection results in a case where the amount of template RNA was increased to 10,000 copies are concurrently shown in Table 2.

TABLE 2

|  |  | Concentration of B3 primer | | | |
|---|---|---|---|---|---|
|  |  | 0.2 μM | 0.4 μM | 0.6 μM | 0.8 μM |
| 10,000 Copies | Detection time (minute) | 9.3 | 9.1 | 9.1 | 9.1 |
| 100 Copies | Detection time (minute) | N.D. | N.D. | 22.3 | N.D. |
|  |  | N.D. | 13.3 | N.D. | 13.4 |
|  |  | 11.5 | 12.8 | N.D. | 12.2 |
|  |  | 14.2 | 12.9 | N.D. | 13.8 |
|  |  | 14.0 | 12.4 | 12.3 | 11.8 |
|  |  | N.D. | 18.6 | N.D. | 13.7 |
|  | Average value | 13.2 | 14.0 | 17.3 | 13.0 |
|  | SD | 1.5 | 2.6 | 7.1 | 0.9 |
|  | CV (%) | 11.5 | 18.4 | 41.1 | 7.1 |
| NC | Detection time (minute) | N.D. | N.D. | N.D. | N.D. |

In the tables in the present specification, SD means a standard deviation, CV means a coefficient of variation, NC means negative control, and N.D. means no detection. In the present test example, cases where quenching of QProbe was not detected within 30 minutes were determined as no detection. As shown in Table 2, the detection sensitivity of the template RNA was not improved by increasing the concentration of the B3 primer.

Example 1

An RT-LAMP reaction was performed (N=2) in the same manner as in Reference Example 1, except that a B4 primer was added to a reaction solution at a final concentration of 0.2 μM. As the B4 primer, the primers shown in Table 3 were used. For comparison, the same reaction was performed without a B4 primer. The results are shown in Table 4. In addition, for reference, detection results in a case where the amount of template RNA was increased to 10,000 copies are concurrently shown in Table 4.

TABLE 3

| B4 Primer | SEQ ID NO. | Sequence (from 5' to 3') | Tm (° C.) |
|---|---|---|---|
| DENV3_B3-m12 | 9 | ATCTAGCCAAGAC | 39.13 |
| DENV3_B3-m13 | 10 | CTAGCCAAGACTC | 40.44 |
| DENV3_B3-m14 | 11 | AGCCAAGACTCCT | 44.96 |
| DENV3_B3-m16 | 12 | GACTTCTTGAAGG | 37.89 |
| DENV3_B3-m18 | 13 | TCTTGAAGGTTCC | 39.79 |
| DENV3_B3-m19 | 14 | TTGAAGGTTCCCC | 43.56 |
| DENV3_B3-m20 | 15 | TTCTTGAAGGTTC | 36.95 |
| DENV3_B3-m21 | 16 | CTTGAAGGTTCCC | 41.53 |
| DENV3_B3-m23 | 17 | AAGGTTCCCCATC | 43.16 |
| DENV3_B3-m25 | 18 | TTGAAGGTTCCCC | 43.56 |
| DENV3_B3-m26 | 19 | GAAGGTTCCCCAT | 43.16 |
| DENV3_B3-m27 | 20 | AGGTTCCCCATCT | 44.34 |

TABLE 4

| | | B4 Primer | | | | | |
|---|---|---|---|---|---|---|---|
| | | None | B3-m12 | B3-m13 | B3-m14 | B3-m16 | B3-m18 | B3-m19 |
| 10,000 Copies | Detection time (min.) | 9.3 | 9.3 | 9.3 | 9.2 | 9.4 | 9.4 | 9.6 |
| 100 Copies | Detection time (min.) | N.D. | 18.7 | 17.3 | 12.3 | 12.3 | 13.5 | 13.3 |
| | | 12.2 | 15.6 | 13.6 | 17.5 | 12.3 | 15.8 | 12.6 |
| | Average value | 12.2 | 17.1 | 15.5 | 14.9 | 12.3 | 14.6 | 12.9 |
| | SD | — | 2.2 | 2.6 | 3.7 | 0.0 | 1.6 | 0.5 |
| | CV (%) | — | 12.6 | 16.9 | 24.8 | 0.2 | 10.9 | 3.8 |
| NC | Detection time (min.) | N.D. | N.D. | N.D. | N.D. | N.D. | N.D. | N.D. |

| | | B4 Primer | | | | | |
|---|---|---|---|---|---|---|---|
| | | B3-m20 | B3-m21 | B3-m23 | B3-m25 | B3-m26 | B3-m27 |
| 10,000 Copies | Detection time (min.) | 9.3 | 9.4 | 9.4 | 9.3 | 9.5 | 9.5 |
| 100 Copies | Detection time (min.) | 17.2 | 12.8 | 15.6 | 13.6 | 13.8 | 13.1 |
| | | 13.8 | 15.5 | 12.2 | 14.7 | 14.7 | 13.2 |
| | Average value | 15.5 | 14.2 | 13.9 | 14.1 | 14.3 | 13.1 |
| | SD | 2.4 | 1.9 | 2.4 | 0.8 | 0.7 | 0.1 |
| | CV (%) | 15.6 | 13.4 | 17.4 | 5.8 | 4.7 | 0.8 |
| NC | Detection time (min.) | N.D. | N.D. | N.D. | N.D. | N.D. | N.D. |

As shown in Table 4, the detection sensitivity of the template RNA was improved by adding the B4 primer.

Example 2

The same RT-LAMP reaction as that in Example 1 was performed with an increased number of times of measurement (N=6). As a B4 primer, B3-m27 was used. For comparison, the same reaction was performed without a B4 primer. The results are shown in Table 5. In addition, for reference, detection results in a case where the amount of template RNA was increased to 10,000 copies are concurrently shown in Table 5.

TABLE 5

| | | B4 Primer | |
|---|---|---|---|
| | | None | B3-m27 |
| 10,000 Copies | Detection time (minute) | 9.6 | 9.5 |
| 100 Copies | Detection time (minute) | N.D. | 13.8 |
| | | 12.6 | 14.3 |
| | | 13.0 | 14.3 |
| | | 13.7 | 11.4 |
| | | 15.1 | 27.4 |
| | | N.D. | 12.5 |
| | Average value | 13.6 | 15.6 |
| | SD | 1.1 | 5.9 |
| | CV (%) | 7.9 | 37.7 |
| NC | Detection time (minute) | N.D. | N.D. |

As shown in Table 5, the increased detection sensitivity due to the addition of the B4 primer was observed even when the number of times of measurement was increased.

Comparative Example 1

The same RT-LAMP reaction as that in Example 1 was performed using F4 primers shown in Table 6 instead of the B4 primers. For comparison, the same reaction was performed without an F4 primer. The results are shown in Table 7. In addition, for reference, detection results in a case where the amount of template RNA was increased to 10,000 copies are concurrently shown in Table 7.

TABLE 6

| F4 Primer | SEQ ID NO. | Sequence (from 5' to 3') | Tm (° C.) |
|---|---|---|---|
| DENV3_F4-1 | 21 | GACTCGGAAGCTT | 44.07 |
| DENV3_F4-2 | 22 | ACTCGGAAGCTTG | 44.53 |
| DENV3_F4-3 | 23 | GACTCGGAAGCTTG | 47.26 |
| DENV3_F4-4 | 24 | GACTCGGAAGCT | 41.69 |
| DENV3_F4-5 | 25 | ACTCGGAAGCTT | 40.70 |
| DENV3_F4-6 | 26 | CTCGGAAGCTTG | 40.54 |

TABLE 7

| | | F4 Primer | | | | | | |
|---|---|---|---|---|---|---|---|---|
| | | None | F4-1 | F4-2 | F4-3 | F4-4 | F4-5 | F4-6 |
| 10,000 Copies | Detection time (minute) | 11.1 | 11.0 | 11.6 | 11.2 | 11.0 | 11.4 | 11.4 |
| 100 Copies | Detection time (minute) | N.D. | 22.1 | 24.7 | 23.4 | N.D. | 26.3 | 18.9 |
| | | 19.3 | N.D. | 22.3 | 24.3 | 20.4 | 20.4 | 15.7 |
| | | 23.9 | 21.7 | 23.2 | N.D. | 19.6 | N.D. | 20.7 |
| | | N.D. | 18.4 | N.D. | N.D. | 25.4 | 18.0 | N.D. |

15

TABLE 7-continued

| | | F4 Primer | | | | | |
|---|---|---|---|---|---|---|---|
| | | None | F4-1 | F4-2 | F4-3 | F4-4 | F4-5 | F4-6 |
| | | N.D. | 18.7 | N.D. | N.D. | 15.1 | N.D. | 19.5 |
| | | N.D. | N.D. | N.D. | N.D. | N.D. | 18.7 | N.D. |
| | Average value | 21.6 | 20.2 | 23.4 | 23.8 | 20.1 | 20.9 | 18.7 |
| | SD | 3.2 | 1.9 | 1.2 | 0.6 | 4.2 | 3.8 | 2.2 |
| | CV (%) | 14.9 | 9.6 | 5.2 | 2.6 | 20.9 | 18.0 | 11.5 |
| NC | Detection time (minute) | N.D. | N.D. | N.D. | N.D. | N.D. | N.D. | N.D. |

As shown in Table 7, the detection sensitivity of the template RNA was not improved by adding the F4 primer.

[Test Example 2] Detection of (–)ssRNA Virus (H5N1)

Reference Example 2

25 µL of a reaction solution having following composition was prepared in a 0.2 mL reagent tube:
20 mM Tricine (pH 8.6),
30 mM KCl,
8 mM MgSO$_4$,
1.4 mM dNTPs,
0.5% Tween 20,
1.6 mM DTT,
1.6 µM FIP Primer and BIP Primer,
0.2 µM F3 Primer and B3 Primer,
0.8 µM Loop Primer F and Loop Primer B,
AMV Reverse Transcriptase 1.0 U (20 U/µL, Manufactured by Roche),
Bst DNA polymerase 22.8 U (Manufactured by New England Biolabs),
RNase Inhibitor (40 U/µL, Manufactured by Promega) 1 µL,
Template RNA (200 copies) 5 µL,
PPase 20 mU (Manufactured by New England Biolabs), and
0.1 µM SYTO 63 Red Fluorescent Nucleic Acid Stain (Manufactured by Thermo Fisher Scientific Inc.).

As an FIP primer, a BIP primer, an F3 primer, a B3 primer, a Loop primer F, and a loop primer B, H5N1-FIP, H5N1-BIP, H5N1-F3v7, H5N1-B3, H5N1-LF, and H5N1-LB shown in Table 8 were respectively used. Template RNA (SEQ ID NO: 27) was prepared by integrating cDNA prepared by RT-PCR from a part of Hemagglutinin (HA) gene of type H5 avian influenza virus (A/Viet Nam/1203/2004 (H5N1), Accession No. AY818135) in to a plasmid, and transcribing and purifying RNA from the plasmid DNA. Script Max Thermo T7 Transcription Kit (manufactured by TOYOBO Co., LTD., Code Number: TSK-101) was used for the transcription, and RNeasy Mini Kit (manufactured by QIAGEN N.V., Catalog Number: No. 74104) was used for RNA purification.

TABLE 8

| Primer | SEQ ID NO. | Sequence (from 5' to 3') | Tm (° C.) |
|---|---|---|---|
| H5N1-F3v7 | 28 | CAATTTTAAAGCCGAATGA | 50.82 |
| H5N1-B3 | 29 | GTCGCAAGGACTAATCT | 51.85 |

16

TABLE 8-continued

| Primer | SEQ ID NO. | Sequence (from 5' to 3') | Tm (° C.) |
|---|---|---|---|
| H5N1-FIP | 30 | ACCATATTCCAACTCACTTTTCAT AATT-TCATTGCACCAGAATATGC | 71.32 |
| H5N1-BIP | 31 | CAAACTCCAATGGGGGC-ATGGTG AGAGGGTGTAT | 74.29 |
| H5N1-LF | 32 | GAGTCCCCTTTCTTGACAAT | 56.69 |
| H5N1-LB | 33 | GATAAACTCTAGTATGCCA | 49.94 |

An RT-LAMP reaction was performed (N=6) at 63° C. for 60 minutes using a real time quantitative PCR system LightCycler (registered trademark) 96 (manufactured by Roche). In addition, the same RT-LAMP reaction was performed (N=6) with the concentration of the F3 primer increased 2 to 4 times. An amplification product of the RT-LAMP reaction was detected by detecting fluorescence of an intercalator (SYTO 63 Red Fluorescent Nucleic Acid Stain) in real time. The results are shown in Table 9. In addition, for reference, detection results in a case where the amount of template RNA was increased to 10,000 copies are concurrently shown in Table 9.

[Table 9]

| | | Concentration of F3 primer | | | |
|---|---|---|---|---|---|
| | | 0.2 µM | 0.4 µM | 0.6 µM | 0.8 µM |
| 10,000 Copies | Detection time (minute) | 7.3 | 7.2 | 7.4 | 7.2 |
| 200 Copies | Detection time (minute) | N.D. | 10.7 | N.D. | N.D. |
| | | N.D. | N.D. | N.D. | N.D. |
| | | 10.7 | 12.6 | 9.7 | 16.8 |
| | | N.D. | N.D. | 27.4 | N.D. |
| | | 11.9 | N.D. | 9.9 | 10.8 |
| | | N.D. | 10.0 | N.D. | 11.7 |
| | Average value | 11.3 | 11.1 | 15.7 | 13.1 |
| | SD | 0.8 | 1.3 | 10.2 | 3.2 |
| | CV (%) | 7.5 | 11.8 | 65.0 | 24.7 |
| NC | Detection time (minute) | N.D. | N.D. | N.D. | N.D. |

In the present test example, in a case where the fluorescence of the intercalator had not been detected within 30 minutes, it was determined as not being detected. As shown in Table 9, the detection sensitivity of the template RNA was not improved by increasing the concentration of the F3 primer.

Example 3

An RT-LAMP reaction was performed (N=6) in the same manner as in Reference Example 2, except that a F4 primer was added to a reaction solution at a final concentration of 0.2 µM. As the F4 primer, the primers shown in Table 10 were used. For comparison, the same reaction was performed without an F4 primer. The results are shown in Table 11. In addition, for reference, detection results in a case where the amount of template RNA was increased to 10,000 copies are concurrently shown in Table 11.

TABLE 10

| F4 Primer | SEQ ID NO. | Sequence (from 5' to 3') | Tm (° C.) |
|---|---|---|---|
| H5N1-F4v2 | 34 | AAAGTGGAAGGA | 35.84 |
| H5N1-F4v6 | 35 | GGGCAAAGTGGA | 42.81 |
| H5N1-F4v7 | 36 | CGGGCAAAGTGG | 45.50 |
| H5N1-F4v17 | 37 | GATTGGTACCAAG | 37.91 |

TABLE 1

| | | F4 Primer | | | | |
|---|---|---|---|---|---|---|
| | | None | F4v2 | F4v6 | F4v7 | F4v17 |
| 10,000 Copies | Detection time (minute) | 7.8 | 7.6 | 7.6 | 7.5 | 8.2 |
| 200 Copies | Detection time (minute) | 10.8 | 10.0 | 10.3 | 9.1 | 11.3 |
| | | 17.6 | 11.5 | 10.2 | 11.4 | 13.0 |
| | | 15.8 | 13.1 | 9.7 | 11.3 | 13.1 |
| | | N.D. | 17.4 | 10.9 | 20.3 | 17.0 |
| | | 10.0 | 26.1 | 9.2 | 25.6 | 9.6 |
| | | N.D. | 11.9 | 11.4 | 17.6 | 11.0 |
| | Average value | 13.5 | 15.0 | 10.3 | 15.9 | 12.5 |
| | SD | 3.7 | 6.0 | 0.8 | 6.4 | 2.5 |
| | CV (%) | 27.5 | 39.9 | 7.7 | 40.1 | 20.3 |
| NC | Detection time (minute) | N.D. | N.D. | N.D. | N.D. | N.D. |

As shown in Table 11, the detection sensitivity of the template RNA was improved by adding the F4 primer.

Comparative Example 2

The same RT-LAMP reaction as that in Example 3 was performed using B4 primers shown in Table 12 instead of the F4 primers. For comparison, the same reaction was performed without a B4 primer. The results are shown in Table 13. In addition, for reference, detection results in a case where the amount of template RNA was increased to 10,000 copies are concurrently shown in Table 13.

TABLE 12

| B4 Primer | SEQ ID NO. | Sequence (from 5' to 3') | Tm (° C.) |
|---|---|---|---|
| H5N1-B4v1 | 38 | TTTCTGAGCCCA | 40.36 |
| H5N1-B4v6 | 39 | GGCTATTTCTGA | 33.65 |
| H5N1-B4v8 | 40 | AGGGCTATTTCT | 34.94 |

TABLE 13

| | | B4 Primer | | | |
|---|---|---|---|---|---|
| | | None | B4v1 | B4v6 | B4v8 |
| 10,000 Copies | Detection time (minute) | 7.9 | 7.8 | 8.5 | 8.1 |
| 200 Copies | Detection time (minute) | 18.9 | 11.3 | 16.6 | 12.2 |
| | | 16.1 | N.D. | 18.0 | N.D. |
| | | N.D. | N.D. | 11.1 | N.D. |
| | | 20.9 | N.D. | N.D. | 11.0 |
| | | N.D. | N.D. | 17.5 | 10.7 |
| | | N.D. | N.D. | N.D. | 10.1 |

TABLE 13-continued

| | | B4 Primer | | | |
|---|---|---|---|---|---|
| | | None | B4v1 | B4v6 | B4v8 |
| | Average value | 18.6 | 11.3 | 15.8 | 11.0 |
| | SD | 2.4 | — | 3.2 | 0.9 |
| | CV (%) | 12.9 | — | 20.3 | 8.2 |
| NC | Detection time (minute) | N.D. | N.D. | N.D. | N.D. |

As shown in Table 13, the detection sensitivity of the template RNA was not improved by adding the B4 primer.

[Test Example 3] Detection of (+)ssRNA Virus (ZIKV)

Reference Example 3

The same RT-LAMP reaction as that in Reference Example 1 of Test Example 1 was performed, except that the template RNA and the primer set were changed as follows. As an FIP primer, a BIP primer, an F3 primer, a B3 primer, a Loop primer F, a loop primer B, and QProbe, ZIKV FIP, ZIKV BIP, ZIKV F3, ZIKV B3, ZIKV LF, ZIKV LB, and ZIKV Qp shown in Table 14 were respectively used. Template RNA (SEQ ID NO: 41) was prepared by integrating cDNA prepared by RT-PCR from NS5 gene of ZIKV into a plasmid, and transcribing and purifying RNA from the plasmid DNA. Script Max Thermo T7 Transcription Kit was used for the transcription, and RNeasy Mini Kit was used for RNA purification. The 3' terminal of QProbe was labeled with BODIPY. The results are shown in Table 15.

TABLE 14

| Primer or probe | SEQ ID NO. | Sequence (from 5' to 3') | Tm (° C.) |
|---|---|---|---|
| ZIKV F3 | 42 | CAGAAGGGACCTCCGACT | 59.37 |
| ZIKV B3 | 43 | CGTAACTGGGGTCTTGTCTT | 58.84 |
| ZIKV FIP | 44 | TTGACCAGGTAGTTCTCCCAGT-ATGGCCAATGCCATTTGTTC | 75.65 |
| ZIKV BIP | 45 | AGGGAGAATGGATGACCACTGA-CTCCTCAATCCACACTCTGT | 76.52 |
| ZIKV LF | 46 | CCCAGTCAACTGGCACAG | 59.51 |
| ZIKV LB | 47 | CATGCTTGTGGTGTG | 50.08 |
| ZIKV Qp | 48 | TGGAACCCAGTCAACTGGCACA GATGAAC-[BODIPY] | 70.54 |

TABLE 15

| | | Concentration of B3 primer | | | |
|---|---|---|---|---|---|
| | | 0.2 μM | 0.4 μM | 0.6 μM | 0.8 μM |
| 10,000 Copies | Detection time (minute) | 8.2 | 7.8 | 8.0 | 7.8 |
| 100 Copies | Detection time (minute) | 15.7 | N.D. | 18.0 | 20.8 |
| | | 12.4 | N.D. | N.D. | 10.2 |
| | | N.D. | N.D. | N.D. | N.D. |
| | | 10.4 | N.D. | N.D. | 15.6 |
| | | 12.8 | 12.6 | N.D. | 13.2 |
| | | 21.7 | N.D. | N.D. | N.D. |

TABLE 15-continued

|  |  | Concentration of B3 primer | | | |
|---|---|---|---|---|---|
|  |  | 0.2 μM | 0.4 μM | 0.6 μM | 0.8 μM |
|  | Average value | 14.6 | 12.6 | 18.0 | 15.0 |
|  | SD | 4.4 | — | — | 4.5 |
|  | CV (%) | 30.2 | — | — | 30.0 |
| NC | Detection time (minute) | N.D. | N.D. | N.D. | N.D. |

As shown in Table 15, the detection sensitivity of the template RNA was not improved by increasing the concentration of the B3 primer.

Example 4

An RT-LAMP reaction was performed (N=6) in the same manner as in Reference Example 3, except that a B4 primer was added to a reaction solution at a final concentration of 0.2 μM. As the B4 primer, the primers shown in Table 16 were used. For comparison, the same reaction was performed without a B4 primer. The results are shown in Table 17. In addition, for reference, detection results in a case where the amount of template RNA was increased to 10,000 copies are concurrently shown in Table 17.

TABLE 16

| B4 Primer | SEQ ID NO | Sequence (from 5' to 3') | Tm (° C.) |
|---|---|---|---|
| ZIKV_B4-3 | 49 | TAGGGAATGTCTGT | 42.47 |
| ZIKV_B4-13 | 50 | GAATGTCTGTCC | 35.68 |
| ZIKV_B4-14 | 51 | TGTCTGTCCATTT | 39.05 |

TABLE 17

|  |  | B4 Primer | | | |
|---|---|---|---|---|---|
|  |  | None | B4-3 | B4-13 | B4-14 |
| 10,000 Copies | Detection time (minute) | 7.0 | 7.1 | 7.5 | 7.1 |
| 100 Copies | Detection time (minute) | 23.7 | 13.0 | 12.0 | 19.2 |
|  |  | N.D. | 12.3 | 11.0 | 11.7 |
|  |  | N.D. | 13.2 | 10.8 | 12.5 |
|  |  | 14.7 | 11.2 | 21.4 | 10.4 |
|  |  | N.D. | 20.0 | 22.4 | 16.8 |
|  |  | N.D. | 15.6 | 10.5 | 11.7 |
|  | Average value | 19.2 | 14.2 | 14.7 | 13.7 |
|  | SD | 6.4 | 3.2 | 5.6 | 3.5 |
|  | CV (%) | 33.2 | 22.4 | 38.3 | 25.3 |
| NC | Detection time (minute) | N.D. | N.D. | N.D. | N.D. |

As shown in Table 17, the detection sensitivity of the template RNA was improved by adding the B4 primer.

Comparative Example 3

The same RT-LAMP reaction as that in Example 4 was performed using F4 primers shown in Table 18 instead of the B4 primers. For comparison, the same reaction was performed without an F4 primer. The results are shown in Table 19. In addition, for reference, detection results in a case where the amount of template RNA was increased to 10,000 copies are concurrently shown in Table 19.

TABLE 18

| F4 Primer | SEQ ID NO. | Sequence (from 5' to 3') | Tm (° C.) |
|---|---|---|---|
| ZIKV_F4-2 | 52 | CTCCTTTATTTCC | 33.98 |
| ZIKV_F4-3 | 53 | AAATCATATGCGCAAAT | 48.21 |

TABLE 19

|  |  | F4 Primer | | |
|---|---|---|---|---|
|  |  | None | F4-2 | F4-3 |
| 10,000 Copies | Detection time (minute) | 7.7 | 7.9 | 7.9 |
| 100 Copies | Detection time (minute) | 12.3 | N.D. | 13.1 |
|  |  | 11.1 | 21.2 | N.D. |
|  |  | N.D. | N.D. | N.D. |
|  |  | N.D. | N.D. | N.D. |
|  |  | 10.5 | N.D. | N.D. |
|  | Average value | 11.3 | 21.2 | 13.1 |
|  | SD | 0.9 | — | — |
|  | CV (%) | 8.1 | — | — |
| NC | Detection time (minute) | N.D. | N.D. | N.D. |

As shown in Table 19, the detection sensitivity of the template RNA was not improved by adding the F4 primer.

[Test Example 4] Detection of (−)ssRNA Virus (RABV)

Reference Example 4

25 L of a reaction solution having following composition was prepared in a 0.2 mL reagent tube:
20 mM Tricine (pH 8.6),
30 mM KCl,
8 mM MgSO$_4$,
1.4 mM dNTPs,
0.5% Tween 20,
1.6 mM DTT,
1.6 μM FIP Primer and BIP Primer,
0.2 μM F3 Primer and B3 Primer,
0.8μ M Loop Primer B,
AMV Reverse Transcriptase 1.0 U (20 U/μL, Manufactured by Roche),
Bst DNA polymerase 22.8 U (Manufactured by New England Biolabs),
RNase Inhibitor (40 U/μL, Manufactured by Promega) 1 μL,
Template RNA (10,000 copies) 5 μL,
PPase 20 mU (Manufactured by New England Biolabs), and
0.1 μM SYTO 63 Red Fluorescent Nucleic Acid Stain (Manufactured by Thermo Fisher Scientific Inc.).
As an FIP primer, a BIP primer, an F3 primer, a B3 primer, and a loop primer B, RABV1-FIP, RABV1-BIP, RABV1-F3, RABV1-B3, and RABV1-LB shown in Table 20 were respectively used. These primers are disclosed in Bazartseren B., S. Inoue, A. Yamada, et al. (2009): Rapid Detection of Rabies Virus by Reverse Transcription Loop-Mediated Isothermal Amplification. Jpn. J. Infect. Dis., 62, 187-191, 2009. Template RNA (SEQ ID NO: 54) was prepared by integrating cDNA prepared by RT-PCR from N gene of RABV into a plasmid, and transcribing and purifying RNA from the plasmid DNA. Script Max Thermo T7 Transcription Kit was used for the transcription, and RNeasy Mini Kit was used for RNA purification.

TABLE 20

| Primer | SEQ ID NO. | Sequence (from 5' to 3') | Tm (° C.) |
|---|---|---|---|
| RABV1-F3 | 55 | ACATGTCCGGAAGACT | 53.62 |
| RABV1-B3 | 56 | CAGACTCAGGAGAAGACC | 54.77 |
| RABV1-FIP | 57 | ACTAGAGAGTTTGGGGTGA-GGACCAGCTATGGAATCC | 73.91 |
| RABV1-BIP | 58 | ACGGGAATTGGGCTCTGAC-CTAAAGATGCATGTTCAG | 73.89 |
| RABV1-LB | 59 | GGCATGGAATTGACAAGGGACC | 63.58 |

An RT-LAMP reaction was performed (N=6) at 63° C. for 60 minutes using a real time quantitative PCR system LightCycler 96. In addition, the same RT-LAMP reaction was performed (N=6) with the concentration of the F3 primer increased 2 to 4 times. An amplification product of the RT-LAMP reaction was detected by detecting fluorescence of an intercalator (SYTO 63 Red Fluorescent Nucleic Acid Stain) in real time. The results are shown in Table 21. In addition, for reference, detection results in a case where the amount of template RNA was increased to $1\times10^6$ copies are concurrently shown in Table 21.

TABLE 21

| | | Concentration of F3 primer | | | |
|---|---|---|---|---|---|
| | | 0.2 µM | 0.4 µM | 0.6 µM | 0.8 µM |
| $1 \times 10^6$ Copies | Detection time (minute) | 18.4 | 17.8 | 18.2 | 17.9 |
| 10,000 Copies | Detection time (minute) | N.D. | 23.2 | 24.2 | 27.4 |
| | | 29.9 | 24.2 | 28.3 | N.D. |
| | | 28.9 | 25.6 | N.D. | 30.0 |
| | | 27.0 | N.D. | 25.6 | 25.3 |
| | | 29.4 | 27.8 | 27.7 | N.D. |
| | | N.D. | 25.3 | 28.1 | N.D. |
| | Average value | 28.8 | 25.2 | 26.8 | 27.6 |
| | SD | 1.3 | 1.7 | 1.8 | 2.3 |
| | CV (%) | 4.5 | 6.8 | 6.8 | 8.5 |
| NC | Detection time (minute) | N.D. | N.D. | N.D. | N.D. |

In the present test example, cases where the fluorescence of the intercalator was not detected within 30 minutes were determined as no detection. As shown in Table 21, the detection sensitivity of the template RNA was not improved by increasing the concentration of the F3 primer.

Example 5

An RT-LAMP reaction was performed (N=6) in the same manner as in Reference Example 4, except that a F4 primer was added to a reaction solution at a final concentration of 0.2 µM. As the F4 primer, the primers shown in Table 22 were used. For comparison, the same reaction was performed without an F4 primer. The results are shown in Table 23. In addition, for reference, detection results in a case where the amount of template RNA was increased to $1\times10^6$ copies are concurrently shown in Table 23.

TABLE 22

| F4 Primer | SEQ ID NO. | Sequence (from 5' to 3') | Tm (° C.) |
|---|---|---|---|
| RABV1-F4v14 | 60 | CAGCAGCAATGCA | 47.00 |

TABLE 23

| | | F4 Primer | |
|---|---|---|---|
| | | None | F4v14 |
| $1 \times 10^6$ Copies | Detection time (minute) | 17.3 | 17.4 |
| 10,000 Copies | Detection time (minute) | 24.8 | 26.6 |
| | | 24.6 | 27.6 |
| | | N.D. | 25.3 |
| | | 28.1 | 26.7 |
| | | 25.1 | 27.7 |
| | | N.D. | 27.3 |
| | Average value | 25.7 | 26.8 |
| | SD | 1.7 | 0.9 |
| | CV (%) | 6.5 | 3.3 |
| NC | Detection time (minute) | N.D. | N.D. |

As shown in Table 23, the detection sensitivity of the template RNA was improved by adding the F4 primer.

Comparative Example 4

The same RT-LAMP reaction as that in Example 5 was performed using B4 primers shown in Table 24 instead of the F4 primers. For comparison, the same reaction was performed without a B4 primer. The results are shown in Table 25. In addition, for reference, detection results in a case where the amount of template RNA was increased to $1\times10^6$ are concurrently shown in Table 25.

TABLE 24

| B4 Primer | SEQ ID NO. | Sequence (from 5' to 3') | Tm (° C.) |
|---|---|---|---|
| RABV1-B4v3 | 61 | TATTTTGCTCAACC | 40.21 |
| RABV1-B4v7 | 62 | TGTCCTGATATTTT | 37.00 |

TABLE 25

| | | B4 Primer | | |
|---|---|---|---|---|
| | | None | B4v3 | B4v7 |
| $1 \times 10^6$ Copies | Detection time (minute) | 21.2 | 20.4 | 19.8 |
| 10,000 Copies | Detection time (minute) | N.D. | N.D. | N.D. |
| | | N.D. | N.D. | N.D. |
| | | 27.5 | N.D. | N.D. |
| | | N.D. | N.D. | N.D. |
| | | N.D. | 28.5 | N.D. |
| | | N.D. | N.D. | N.D. |
| | Average value | 27.5 | 28.5 | — |
| | SD | — | — | — |
| | CV (%) | — | — | — |
| NC | Detection time (minute) | N.D. | N.D. | N.D. |

As shown in Table 25, the detection sensitivity of the template RNA was not improved by adding the B4 primer.

The invention claimed is:

1. A method for detecting a single-stranded RNA virus in a sample, the method comprising:

bringing a primer set into contact with a sample to perform a reverse transcription loop-mediated isothermal amplification reaction, wherein the primer set is designed based on a nucleotide sequence of a target RNA of a single-stranded RNA virus and a nucleotide sequence of a nucleic acid complementary to the target RNA, wherein the primer set comprises following (i) to (v):

(i) an FIP primer having the same nucleotide sequence as the region F1c at a 5' terminal and having the same nucleotide sequence as the region F2 at a 3' terminal;

(ii) a BIP primer having the same nucleotide sequence as the region B1c at a 5' terminal and having the same nucleotide sequence as the region B2 at a 3' terminal;

(iii) an F3 primer which is an outer primer having the same nucleotide sequence as the region F3;

(iv) a B3 primer which is an outer primer having the same nucleotide sequence as the region B3; and (v) one additional outer primer, wherein either (a) or (b):

(a) the single-stranded RNA virus is a plus-strand single-stranded RNA virus, the target RNA comprises the arbitrary regions F3, F2, F1, B1c, B2c, B3c, and B4c in this order in the direction from the 5' terminal to 3' terminal, wherein the nucleic acid complementary to the target RNA comprises the arbitrary regions F3c, F2c, F1c, B1, B2, B3, and B4 in this order in the direction from 3' terminal to 5' terminal, and the one additional outer primer has a nucleotide sequence present on 5' terminal side from the region B4 in the nucleic acid complementary to the target RNA; or (b) the single-stranded RNA virus is a minus-strand single-stranded RNA virus, the target RNA comprises the arbitrary regions F4c, F3c, F2c, F1c, B1, B2, and B3 in this order in the direction from 3' terminal to 5' terminal, the nucleic acid complementary to the target RNA comprises the arbitrary regions F4, F3, F2, F1, B1c, B2c, and B3c in this order in the direction from the 5' terminal to 3' terminal, and the one additional outer primer has a nucleotide sequence present on 5' terminal side from the region F4 in the nucleic acid complementary to the target RNA, and wherein uracil that may be present in the nucleotide sequences of the FIP primer, the BIP primer, the F3 primer, the B3 primer, and the one additional outer primer may be substituted with thymine.

2. The method according to claim 1, wherein the primer set further comprises:

(vi) a loop primer F having the same nucleotide sequence as an arbitrary region between the region F1c and the region F2c; and (vii) a loop primer B having the same nucleotide sequence as an arbitrary region between the region B1c and the region B2c, and wherein uracil that may be present in the nucleotide sequences of the loop primer F and the loop primer B may be substituted with thymine.

3. The method according to claim 1, wherein a melting temperature of the one additional outer primer of (v) is 30° C. to 55° C.

4. The method according to claim 1, the method further comprising:

detecting an amplification product of the reverse transcription loop-mediated isothermal amplification reaction.

* * * * *